US012606640B2

(12) United States Patent
Garcia Fruitos et al.

(10) Patent No.: US 12,606,640 B2
(45) Date of Patent: Apr. 21, 2026

(54) RECOMBINANT ANTIMICROBIAL MULTIDOMAIN POLYPEPTIDE, METHODS OF PRODUCING AND USES THEREOF

(71) Applicant: IRTA, INSTITUT DE RECERCA I TRANSFERENCIA AGROALIMENTARIES, Caldes de Montbui (ES)

(72) Inventors: Elena Garcia Fruitos, Caldes de Montbui (ES); Anna Aris Giralt, Caldes de Montbui (ES); Ramon Roca Pinilla, Caldes de Montbui (ES); Adria Lopez Cano, Caldes de Montbui (ES)

(73) Assignee: IRTA, INSTITUT DE RECERCA I TRANSFERÈNCIA AGROALIMENTÀRIES, Caldes de Montbui (ES)

( * ) Notice: Subject to any disclaimer, the term of this patent is extended or adjusted under 35 U.S.C. 154(b) by 796 days.

(21) Appl. No.: 17/432,474

(22) PCT Filed: Feb. 18, 2020

(86) PCT No.: PCT/EP2020/054235

§ 371 (c)(1),
(2) Date: Aug. 19, 2021

(87) PCT Pub. No.: WO2020/169602

PCT Pub. Date: Aug. 27, 2020

(65) Prior Publication Data

US 2022/0289867 A1     Sep. 15, 2022

(30) Foreign Application Priority Data

Feb. 19, 2019    (EP) ..................................... 19382115

(51) Int. Cl.
C07K 19/00        (2006.01)
C12N 15/63        (2006.01)

(52) U.S. Cl.
CPC .............. C07K 19/00 (2013.01); C12N 15/63 (2013.01); *C07K 2319/035* (2013.01); *C07K 2319/21* (2013.01); *C07K 2319/33* (2013.01); *C07K 2319/50* (2013.01)

(58) Field of Classification Search
CPC ................ C07K 19/00; C07K 2319/50; C07K 2319/33; C07K 2319/035; C07K 2319/21; C12N 15/63; A61K 38/00
See application file for complete search history.

(56) References Cited

U.S. PATENT DOCUMENTS 8,003,348 B2      8/2011  Kim et al.

FOREIGN PATENT DOCUMENTS

WO      WO 2008/030988 A2      3/2008
WO      WO 2014/078373 A1      5/2014

OTHER PUBLICATIONS

Wu WY, Mee C, Califano F, Banki R, Wood OW. Recombinant protein purification by self-cleaving aggregation tag. Nat Protoc. 2006;1(5):2257-62. doi: 10.1038/nprot.2006.314. PMID: 17406465. (Year: 2006).*
Bucki, Robert, et al. "Extracellular gelsolin binds lipoteichoic acid and modulates cellular response to proinflammatory bacterial wall components." The Journal of Immunology 181.7 (2008): 4936-4944. (Year: 2008).*
International Search Report and Written Opinion issued for PCT Application No. PCT/EP2020/054235, 21 pages.
Anonymous: "Gelsolin, actin-depolymerizing factor", Feb. 13, 2019; XP055674542 retrieved from the Internet: URL:https://www.uniprot.org/uniprot/P06396.txt?version=228 [retrieved on Jun. 30, 2020].
De Smet, et al: "Human antimicrobial peptides: defensins, cathelicidins and histatins" Biotechnology Letters 2005; vol. 27(18), pp. 1337-1347.
Hwang, et al: "Targeted expression, purification, and cleavage of fusion proteins from inclusion bodies in Escherichia coli", FEBS Letters 2014 (published online Sep. 27, 2013); vol. 588(2), pp. 247-252; XP028669968.
Kim, et al: "Enhancement of the antimicrobial activity and selectivity of GNU7 against Gram-negative bacteria by fusion with LPS-targeting peptide", Peptides; May 27, 2016; vol. 82, pp. 60-66; XP029645390.
Li: "Recombinant production of antimicrobial peptides in *Escherichia coli*: A review", Protein Expression and Purification 2011, vol. 80(2), pp. 260-267.
Peternel, et al: "Engineering inclusion bodies for non denaturing extraction of functional proteins" Microbial Cell Factories, BioMed Central; Dec. 1, 2008; vol. 7(34), pp. 1-9.

(Continued)

*Primary Examiner* — Sean C. Barron
(74) *Attorney, Agent, or Firm* — Squire Patton Boggs (US) LLP

(57)        ABSTRACT

A novel recombinant antimicrobial multidomain polypeptide in an aggregated and functional format is provided. The antimicrobial multidomain polypeptide comprises at least three peptidic domains: a) a non-enzymatic antimicrobial peptidic domain from mammal's immune system, b) a bacterial binding peptidic domain which interacts with the bacterial cell wall or membrane, and c) an enzymatic antimicrobial peptidic domain from mammal's immune system. The antimicrobial multidomain polypeptide exhibits a broad-spectrum antimicrobial effect and is produced in an efficient production system, i.e in form of inclusion bodies.

21 Claims, 9 Drawing Sheets

Specification includes a Sequence Listing.

(56) References Cited

OTHER PUBLICATIONS

Orrapin, et al: "Recombinant expression of novel protegrin-1 dimer and LL-37-linker-histatin-5 hybrid peptide mediated biotin carboxyl carrier protein fusion partner", Protein Expression and Purification 2014 (published online Oct. 29, 2013); vol. 93, pp. 46-53; XP055594532.

Unzueta, et al: "Intracellular CXCR4 + cell targeting with T22-empowered protein-only nanoparticles" International Journal of Nanomedicine 2012; vol. 7, pp. 4533-4544.

Vazquez, et al: "Functional Inclusion Bodies Produced in Bacteria as Naturally Occurring Nanopills for Advanced Cell Therapies", Advanced Materials; Apr. 3, 2012; vol. 24(13), pp. 1742-1747; XP055593274.

Yasin, et al., "Susceptibility of Chlamydia trachomatis to Protegrins and Defensins," Infect Immun. Mar. 1996; vol. 64, No. 3, pp. 709-713. doi: 10.1128/iai.64.3.709-713.1996. PMID: 8641770; PMCID: PMC173826.

Cunningham, et al., "Cell Permeant Polyphosphoinositide-binding Peptides That Block Cell Motility and Actin Assembly," J Biol Chem. Nov. 16, 2001, vol. 276, No. 46, pp. 43390-43399. doi: 10.1074/jbc.M105289200. Epub Aug. 30, 2001. PMID: 11533030.

* cited by examiner

| ST | IAMF1 Y | P | % AG |
|---|---|---|---|
| BL21 (DE3) | 96.5 mg/L | 95 % | 74 |

| ST | IAMF1 Y | P |
|---|---|---|
| BL21 (DE3) | 0.67 mg/L | 93 % |

| ST | JAMF2 Y | P | % AG |
|---|---|---|---|
| BL21 (DE3) | 179.2 mg/L | 92 % | 88 |

| ST | JAMF2 Y | P |
|---|---|---|
| BL21 (DE3) | 0.34 mg/L | 89 % |

SEQUENCE LISTING

```
<160> NUMBER OF SEQ ID NOS: 18

<210> SEQ ID NO 1
<211> LENGTH: 8
<212> TYPE: PRT
<213> ORGANISM: Artificial Sequence
<220> FEATURE:
<223> OTHER INFORMATION: Linker sequence

<400> SEQUENCE: 1

Ser Gly Gly Gly Ser Gly Gly Ser
1               5

<210> SEQ ID NO 2
<211> LENGTH: 62
<212> TYPE: PRT
<213> ORGANISM: Homo sapiens

<400> SEQUENCE: 2

Arg Lys Arg Met Arg Asn Arg Ile Ala Ala Ser Lys Cys Arg Lys Arg
1               5                   10                  15

Lys Leu Glu Arg Ile Ala Arg Leu Glu Glu Lys Val Lys Thr Leu Lys
            20                  25                  30

Ala Gln Asn Ser Glu Leu Ala Ser Thr Ala Asn Met Leu Arg Glu Gln
        35                  40                  45

Val Ala Gln Leu Lys Gln Lys Val Met Asn His Val Asn Ser
    50                  55                  60

<210> SEQ ID NO 3
<211> LENGTH: 94
<212> TYPE: PRT
<213> ORGANISM: Homo sapiens

<400> SEQUENCE: 3

Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
                85                  90

<210> SEQ ID NO 4
<211> LENGTH: 10
<212> TYPE: PRT
<213> ORGANISM: Homo sapiens

<400> SEQUENCE: 4
```

```
Gln Arg Leu Phe Gln Val Lys Gly Arg Arg
1               5                   10

<210> SEQ ID NO 5
<211> LENGTH: 189
<212> TYPE: PRT
<213> ORGANISM: Homo sapiens

<400> SEQUENCE: 5

Met Ala Leu Leu Ser Arg Pro Ala Leu Thr Leu Leu Leu Leu Leu Met
1               5                   10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln His Asp Arg
                100                 105                 110

Cys Tyr Glu Thr Cys Gly Lys Ser Lys Asn Asp Cys Asp Glu Glu Phe
            115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175

Ala Ala Cys Arg Cys His Tyr Glu Glu Lys Thr Asp Leu
                180                 185

<210> SEQ ID NO 6
<211> LENGTH: 93
<212> TYPE: PRT
<213> ORGANISM: Homo sapiens

<400> SEQUENCE: 6

Gly Arg Ala Gln Ser Ile Gly Arg Arg Gly Lys Val Glu Gln Leu Ser
1               5                   10                  15

Pro Glu Glu Glu Glu Lys Arg Arg Ile Arg Arg Glu Arg Asn Lys Met
            20                  25                  30

Ala Ala Ala Lys Cys Arg Asn Arg Arg Glu Leu Thr Asp Thr Leu
        35                  40                  45

Gln Ala Glu Thr Asp Gln Leu Glu Asp Glu Lys Ser Ala Leu Gln Thr
    50                  55                  60

Glu Ile Ala Asn Leu Leu Lys Glu Lys Glu Lys Leu Glu Phe Ile Leu
65                  70                  75                  80

Ala Ala His Arg Pro Ala Cys Lys Ile Pro Asp Asp Leu
                85                  90

<210> SEQ ID NO 7
<211> LENGTH: 6
<212> TYPE: PRT
<213> ORGANISM: Artificial Sequence
```

<220> FEATURE:
<223> OTHER INFORMATION: His Tag H6

<400> SEQUENCE: 7

His His His His His His
1               5

<210> SEQ ID NO 8
<211> LENGTH: 32
<212> TYPE: PRT
<213> ORGANISM: Homo sapiens

<400> SEQUENCE: 8

Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
                20                  25                  30

<210> SEQ ID NO 9
<211> LENGTH: 167
<212> TYPE: PRT
<213> ORGANISM: Homo sapiens

<400> SEQUENCE: 9

Gln Glu Gln Ala Gln Thr Thr Asp Trp Arg Ala Thr Leu Lys Thr Ile
1               5                   10                  15

Arg Asn Gly Val His Lys Ile Asp Thr Tyr Leu Asn Ala Ala Leu Asp
                20                  25                  30

Leu Leu Gly Gly Glu Asp Gly Leu Cys Gln Tyr Lys Cys Ser Asp Gly
            35                  40                  45

Ser Lys Pro Phe Pro Arg Tyr Gly Tyr Lys Pro Ser Pro Pro Asn Gly
        50                  55                  60

Cys Gly Ser Pro Leu Phe Gly Val His Leu Asn Ile Gly Ile Pro Ser
65                  70                  75                  80

Leu Thr Lys Cys Cys Asn Gln His Asp Arg Cys Tyr Glu Thr Cys Gly
                85                  90                  95

Lys Ser Lys Asn Asp Cys Asp Glu Glu Phe Gln Tyr Cys Leu Ser Lys
                100                 105                 110

Ile Cys Arg Asp Val Gln Lys Thr Leu Gly Leu Thr Gln His Val Gln
            115                 120                 125

Ala Cys Glu Thr Thr Val Glu Leu Leu Phe Asp Ser Val Ile His Leu
        130                 135                 140

Gly Cys Lys Pro Tyr Leu Asp Ser Gln Arg Ala Ala Cys Arg Cys His
145                 150                 155                 160

Tyr Glu Glu Lys Thr Asp Leu
                165

<210> SEQ ID NO 10
<211> LENGTH: 486
<212> TYPE: PRT
<213> ORGANISM: Artificial Sequence
<220> FEATURE:
<223> OTHER INFORMATION: JAMF1

<400> SEQUENCE: 10

Arg Lys Arg Met Arg Asn Arg Ile Ala Ala Ser Lys Cys Arg Lys Arg
1               5                   10                  15

Lys Leu Glu Arg Ile Ala Arg Leu Glu Glu Lys Val Lys Thr Leu Lys
                20                  25                  30

```
Ala Gln Asn Ser Glu Leu Ala Ser Thr Ala Asn Met Leu Arg Glu Gln
        35                  40                  45

Val Ala Gln Leu Lys Gln Lys Val Met Asn His Val Asn Ser Ser Gly
    50                  55                  60

Gly Gly Ser Gly Gly Ser Met Arg Thr Ile Ala Ile Leu Ala Ala Ile
65                  70                  75                  80

Leu Leu Val Ala Leu Gln Ala Gln Ala Glu Ser Leu Gln Glu Arg Ala
                85                  90                  95

Asp Glu Ala Thr Thr Gln Lys Gln Ser Gly Glu Asp Asn Gln Asp Leu
                100                 105                 110

Ala Ile Ser Phe Ala Gly Asn Gly Leu Ser Ala Leu Arg Thr Ser Gly
            115                 120                 125

Ser Gln Ala Arg Ala Thr Cys Tyr Cys Arg Thr Gly Arg Cys Ala Thr
    130                 135                 140

Arg Glu Ser Leu Ser Gly Val Cys Glu Ile Ser Gly Arg Leu Tyr Arg
145                 150                 155                 160

Leu Cys Cys Arg Ser Gly Gly Gly Ser Gly Gly Ser Gln Arg Leu Phe
                165                 170                 175

Gln Val Lys Gly Arg Arg Ser Gly Gly Gly Ser Gly Gly Ser Met Ala
            180                 185                 190

Leu Leu Ser Arg Pro Ala Leu Thr Leu Leu Leu Leu Met Ala Ala
            195                 200                 205

Val Val Arg Cys Gln Glu Gln Ala Gln Thr Thr Asp Trp Arg Ala Thr
    210                 215                 220

Leu Lys Thr Ile Arg Asn Gly Val His Lys Ile Asp Thr Tyr Leu Asn
225                 230                 235                 240

Ala Ala Leu Asp Leu Leu Gly Gly Glu Asp Gly Leu Cys Gln Tyr Lys
            245                 250                 255

Cys Ser Asp Gly Ser Lys Pro Phe Pro Arg Tyr Gly Tyr Lys Pro Ser
            260                 265                 270

Pro Pro Asn Gly Cys Gly Ser Pro Leu Phe Gly Val His Leu Asn Ile
            275                 280                 285

Gly Ile Pro Ser Leu Thr Lys Cys Cys Asn Gln His Asp Arg Cys Tyr
    290                 295                 300

Glu Thr Cys Gly Lys Ser Lys Asn Asp Cys Asp Glu Glu Phe Gln Tyr
305                 310                 315                 320

Cys Leu Ser Lys Ile Cys Arg Asp Val Gln Lys Thr Leu Gly Leu Thr
            325                 330                 335

Gln His Val Gln Ala Cys Glu Thr Thr Val Glu Leu Leu Phe Asp Ser
            340                 345                 350

Val Ile His Leu Gly Cys Lys Pro Tyr Leu Asp Ser Gln Arg Ala Ala
    355                 360                 365

Cys Arg Cys His Tyr Glu Glu Lys Thr Asp Leu Ser Gly Gly Gly Ser
    370                 375                 380

Gly Gly Ser Gly Arg Ala Gln Ser Ile Gly Arg Arg Gly Lys Val Glu
385                 390                 395                 400

Gln Leu Ser Pro Glu Glu Glu Glu Lys Arg Arg Ile Arg Arg Glu Arg
            405                 410                 415

Asn Lys Met Ala Ala Ala Lys Cys Arg Asn Arg Arg Arg Glu Leu Thr
            420                 425                 430

Asp Thr Leu Gln Ala Glu Thr Asp Gln Leu Glu Asp Glu Lys Ser Ala
            435                 440                 445

Leu Gln Thr Glu Ile Ala Asn Leu Leu Lys Glu Lys Glu Lys Leu Glu
```

-continued

```
          450                    455                    460

Phe Ile Leu Ala Ala His Arg Pro Ala Cys Lys Ile Pro Asp Asp Leu
465                    470                    475                    480

His His His His His His
                  485

<210> SEQ ID NO 11
<211> LENGTH: 402
<212> TYPE: PRT
<213> ORGANISM: Artificial Sequence
<220> FEATURE:
<223> OTHER INFORMATION: JAMF2

<400> SEQUENCE: 11

Arg Lys Arg Met Arg Asn Arg Ile Ala Ala Ser Lys Cys Arg Lys Arg
1                   5                    10                   15

Lys Leu Glu Arg Ile Ala Arg Leu Glu Glu Lys Val Lys Thr Leu Lys
                  20                   25                   30

Ala Gln Asn Ser Glu Leu Ala Ser Thr Ala Asn Met Leu Arg Glu Gln
             35                   40                   45

Val Ala Gln Leu Lys Gln Lys Val Met Asn His Val Asn Ser Ser Gly
        50                   55                   60

Gly Gly Ser Gly Gly Ser Ala Thr Cys Tyr Cys Arg Thr Gly Arg Cys
65                   70                   75                   80

Ala Thr Arg Glu Ser Leu Ser Gly Val Cys Glu Ile Ser Gly Arg Leu
                  85                   90                   95

Tyr Arg Leu Cys Cys Arg Ser Gly Gly Gly Ser Gly Gly Ser Gln Arg
                  100                  105                  110

Leu Phe Gln Val Lys Gly Arg Arg Ser Gly Gly Gly Ser Gly Gly Ser
             115                  120                  125

Gln Glu Gln Ala Gln Thr Thr Asp Trp Arg Ala Thr Leu Lys Thr Ile
             130                  135                  140

Arg Asn Gly Val His Lys Ile Asp Thr Tyr Leu Asn Ala Ala Leu Asp
145                  150                  155                  160

Leu Leu Gly Gly Glu Asp Gly Leu Cys Gln Tyr Lys Cys Ser Asp Gly
                  165                  170                  175

Ser Lys Pro Phe Pro Arg Tyr Gly Tyr Lys Pro Ser Pro Pro Asn Gly
             180                  185                  190

Cys Gly Ser Pro Leu Phe Gly Val His Leu Asn Ile Gly Ile Pro Ser
             195                  200                  205

Leu Thr Lys Cys Cys Asn Gln His Asp Arg Cys Tyr Glu Thr Cys Gly
        210                  215                  220

Lys Ser Lys Asn Asp Cys Asp Glu Glu Phe Gln Tyr Cys Leu Ser Lys
225                  230                  235                  240

Ile Cys Arg Asp Val Gln Lys Thr Leu Gly Leu Thr Gln His Val Gln
                  245                  250                  255

Ala Cys Glu Thr Thr Val Glu Leu Leu Phe Asp Ser Val Ile His Leu
                  260                  265                  270

Gly Cys Lys Pro Tyr Leu Asp Ser Gln Arg Ala Ala Cys Arg Cys His
             275                  280                  285

Tyr Glu Glu Lys Thr Asp Leu Ser Gly Gly Gly Ser Gly Gly Ser Gly
        290                  295                  300

Arg Ala Gln Ser Ile Gly Arg Arg Gly Lys Val Glu Gln Leu Ser Pro
305                  310                  315                  320

Glu Glu Glu Glu Lys Arg Arg Ile Arg Arg Glu Arg Asn Lys Met Ala
```

```
                    325                 330                 335

Ala Ala Lys Cys Arg Asn Arg Arg Arg Glu Leu Thr Asp Thr Leu Gln
            340                 345                 350

Ala Glu Thr Asp Gln Leu Glu Asp Glu Lys Ser Ala Leu Gln Thr Glu
        355                 360                 365

Ile Ala Asn Leu Leu Lys Glu Lys Glu Lys Leu Glu Phe Ile Leu Ala
    370                 375                 380

Ala His Arg Pro Ala Cys Lys Ile Pro Asp Asp Leu His His His His
385                 390                 395                 400

His His

<210> SEQ ID NO 12
<211> LENGTH: 8
<212> TYPE: PRT
<213> ORGANISM: Artificial Sequence
<220> FEATURE:
<223> OTHER INFORMATION: Aggregation tag GFIL8

<400> SEQUENCE: 12

Gly Phe Ile Leu Gly Phe Ile Leu
1               5

<210> SEQ ID NO 13
<211> LENGTH: 16
<212> TYPE: PRT
<213> ORGANISM: Artificial Sequence
<220> FEATURE:
<223> OTHER INFORMATION: Aggregation tag GFIL16

<400> SEQUENCE: 13

Gly Phe Ile Leu Gly Phe Ile Leu Gly Phe Ile Leu Gly Phe Ile Leu
1               5                   10                  15

<210> SEQ ID NO 14
<211> LENGTH: 18
<212> TYPE: PRT
<213> ORGANISM: Artificial Sequence
<220> FEATURE:
<223> OTHER INFORMATION: Aggregation tag alpha helical peptide 18A

<400> SEQUENCE: 14

Glu Trp Leu Lys Ala Phe Tyr Glu Lys Val Leu Glu Lys Leu Lys Glu
1               5                   10                  15

Leu Phe

<210> SEQ ID NO 15
<211> LENGTH: 16
<212> TYPE: PRT
<213> ORGANISM: Artificial Sequence
<220> FEATURE:
<223> OTHER INFORMATION: Aggregation tag beta-strand peptide ELK16

<400> SEQUENCE: 15

Leu Glu Leu Glu Leu Lys Leu Lys Leu Glu Leu Glu Leu Lys Leu Lys
1               5                   10                  15

<210> SEQ ID NO 16
<211> LENGTH: 8
<212> TYPE: PRT
<213> ORGANISM: Artificial Sequence
<220> FEATURE:
<223> OTHER INFORMATION: Aggregation tag surfactant-like peptide L6KD

<400> SEQUENCE: 16
```

-continued

```
Leu Leu Leu Leu Leu Leu Lys Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Aggregation tag L6K2

<400> SEQUENCE: 17

Leu Leu Leu Leu Leu Leu Lys Lys
1               5

<210> SEQ ID NO 18
<211> LENGTH: 8
<212> TYPE: PRT
<213> ORGANISM: Artificial Sequence
<220> FEATURE:
<223> OTHER INFORMATION: Aggregation tag DKL6

<400> SEQUENCE: 18

Asp Lys Leu Leu Leu Leu Leu Leu
1               5
```

RECOMBINANT ANTIMICROBIAL MULTIDOMAIN POLYPEPTIDE, METHODS OF PRODUCING AND USES THEREOF

CROSS REFERENCE TO RELATED APPLICATION

The present application is a 35 USC 371 national phase filing of PCT/EP2020/054235 filed on Feb. 18, 2020, which claims the benefit of and priority to European Patent Application EP19382115.4 filed on Feb. 19, 2019, both applications are incorporated herein by reference in their entirety.

INCORPORATION BY REFERENCE

The present application contains a Sequence Listing which has been submitted in ASCII format via Patent Center and is hereby incorporated by reference in its entirety. Said ASCII copy having been modified on Oct. 31, 2025, is named "108663_00279_Corrected_SequenceListing.txt" and is 16,023 bytes in size.

FIELD OF THE INVENTION

The present invention refers to the field of medicine and particularly, to novel antimicrobial agents. It refers to a recombinant antimicrobial multidomain polypeptide in an aggregated and functional format, methods of producing as well as several applications thereof.

BACKGROUND ART

The increasing prevalence of antibiotic-resistant pathogens is a pressing healthcare challenge. Strategies based on biomolecules synthesized by innate immunity such as host defense peptides are gaining strength as one potential solution.

Host Defense Peptides (HDPs), also known as antimicrobial peptides (AMPs), are cationic amphiphilic peptides synthesized by nearly all multicellular organisms able to kill bacteria through the disruption of their basic cell wall structures. These positively charged peptides have bactericidal broad-spectrum activity since their action is based on their interaction and disruption of negatively charged bacterial cell envelope.

However, despite HDPs show promising therapeutic activities, their high susceptibility to proteolytic degradation by microbial and host enzymes (short half-life), their in vivo toxicity (high doses needed), and also, the high production costs are important drawbacks that largely hinder their final in vivo application. Aiming to address some of these major concerns, synthetic peptidomimetics mimicking HDPs have been developed. Although these peptides are biologically active against multidrug-resistant bacteria and show an improved stability, they still present important toxic effects and large production costs for in vivo administration of its soluble form.

Although most of the AMPs, being relatively short, are produced by chemical synthesis, several AMPs have been produced using recombinant technology. However, one of the mayor problems is that by its antimicrobial nature, the AMP is also cytotoxic for the producer cell, and depending on the size it can be easily degraded. To address such concerns, some AMPs are produced as part of a recombinant fusion protein, linked to a carrier that stabilizes the peptide. Some examples of carriers to produce are SUMO (Small Ubiquitin-like Modifier), thioredoxin, GST (Glutathione S Transferase), and human serum albumin.

Another approach described in U.S. Pat. No. 8,003,348 B2 is linking the AMP to an acidic peptide, so that the charge-charge interaction simultaneously with the expression neutralizes the potential cytotoxicity of the antimicrobial peptide, resulting in prevention of antimicrobial peptide-mediated killing of host microorganisms.

Other approaches aim to improve the antimicrobial action of the AMPs. For instance, WO2008030988 A2 describes a targeting peptide capable of specifically binding to *Pseudomonas aeruginosa* and *Streptococcus mutans*, linked to an antimicrobial peptide by means of a linker. Both peptides (i.e. the targeting peptide and the antimicrobial peptide) are synthetically produced.

Furthermore, a naked molecule (natural or biological) mimicking what host defense does in front of a bacterial infection is not sufficient to develop efficient antimicrobials. In this context, nanobiotechnology represents a promising opportunity to overcome these drawbacks allowing the design of nanocarriers to encapsulate biomolecules for drug delivery to ultimately improve their stability and in vivo efficacy, over-coming dosage problems and, in consequence, its associated toxicity. Besides, the encapsulation of drugs allows a targeted delivery to the cell or tissue of interest. However, it should also be mentioned that the composition of these nanocarriers greatly influence on their final toxicity, being extremely important to develop safe carriers for delivery purposes. On the other hand, the preparation of nanoparticles needs a three-step process, being necessary to produce the carriers and the biomolecule separately, to be finally encapsulated in a last step, which is a process with important associated costs.

WO2014078373 A1 describes an antigen binding protein which is an antibody binding to *Staphylococcus aureus* antigen fused to one or two microbiocides or antimicrobial peptides, that can be enzymatic (e.g. peptidoglycan hydrolase including lysosthapin) or nonenzymatic (e.g. defensin or cathelicidin). Inclusion bodies are not disclosed.

It is difficult to understand the specific constructs that are experimentally tested in this document, but it can be concluded from FIGS. 3-5 that the constructs showing antimicrobial activity are those forming a complete antibody (two heavy and two lightchains) each one linked to one microbiocide. The constructs shown in FIGS. 3-5 formed by just one heavy or light chain linked to one microbiocide are not functional. Thus, the antigen binding protein with antimicrobial activity disclosed in this document is a complex molecule (antibody formed by sequences with disulphide bridges).

Due to this fact, the antigen binding protein is produced in eukaryotic cells using a retrovector construct and CHO cells (page 56 line 28 to page 57 line 10). Thus, starting from this document, the inclusion bodies technology is neither derivable nor applicable.

On the other hand, the antigen binding protein has been designed to specifically target *Staphylococcus aureus* and therefore the microbiocide domains accompanying the main molecule (i.e. the antibody) are only effective against this pathogen. Reversely, the antimicrobial multidomain polypeptide of the invention has demonstrated a broad-spectrum antimicrobial effect, attacking both Gram negative and Gram positive bacteria (as shown in the provided Examples).

Orrapin S. et al., 2013 describes a fusion protein comprising (1) the biotin carboxyl carrier protein (BCCP) which is a carrier protein such as SUMO, commonly used in the art to stabilize the protein and reduce toxicity; (2) a dimeric form of porcine protegrin-1 (PG-1), which is a non-enzymatic peptidic domain; (3) LL-37, which is also a non-enzymatic peptidic domain; and (4) histatin-5, which is also a non-enzymatic peptidic domain. Therefore, the fusion protein described in Orrapin comprises three non-enzymatic peptidic domains plus a carrier protein.

It is noted that PG-1 cannot be considered a targeting moiety or a bacterial binding peptidic domain as used in the present invention. PG-1 is widely described as a member of AMP family, which is characterized to be cathionic peptides able to break bacterial cell wall. PG1 needs to bind to LPS in order to disrupt the cell wall. Contrarily, a bacterial binding peptidic domain as used in the present invention (e.g. gelsolin) only binds to the bacterial cells without having any further effect.

It is also noted that the fusion protein that comprises three non-enzymatic peptidic domains plus a carrier protein described in Orrapin is not the final protein but an intermediate construct that allows to efficiently produced AMPs. The objective of Orrapin is producing on one hand a PG-1 dimer and on the other hand LL-37 fused to histatin-5 to be used as separate antimicrobial peptides. Thus, the final product is not a single polypeptide with all the domains mentioned before, but on one hand, a PG-1 dimer (which is a non-enzymatic AMP) and on the other hand, LL-37 fused to histatin-5, i.e. a fusion protein formed with two non-enzymatic AMPs. These two products are obtained after applying protein cleavage to the expressed fusion protein.

In Orrapin, the antimicrobial activity of said "short" peptides is separately tested in FIG. 7. The authors do not test all the domains combined in a single polypeptide, differently from the present invention.

Therefore, Orrapin describes the construct comprising all the domains described above in a single polypeptide, just as a strategy to produce the final AMP products described before.

The above-mentioned drawbacks together with price, stability, toxicity, effectiveness and delivery appear to be key parameters in the development of a new generation of antimicrobial agents.

SUMMARY OF THE INVENTION

One problem to be solved by the present invention may be seen as related to the provision of antimicrobial agents with enhanced antimicrobial properties.

The solution is based on the provision of a recombinant antimicrobial multidomain polypeptide in an aggregated and functional format as a new generation of antimicrobial molecules. The invention provides recombinant antimicrobial multidomain polypeptides, methods of producing as well as several applications thereof.

Accordingly, a first aspect of the invention relates to a recombinant antimicrobial multidomain polypeptide comprising at least three peptidic domains, wherein each peptidic domain is selected from the group consisting of:
- a) a non-enzymatic antimicrobial peptidic domain from mammal's immune system,
- b) a bacterial binding peptidic domain which interacts with the bacterial cell wall or membrane, and
- c) an enzymatic antimicrobial peptidic domain from mammal's immune system, wherein the antimicrobial multidomain polypeptide is in form of inclusion bodies (hereinafter referred as "IBs").

A second aspect relates to a recombinant antimicrobial multidomain polypeptide comprising at least three peptidic domains:
- a) a non-enzymatic antimicrobial peptidic domain from mammal's immune system,
- b) a bacterial binding peptidic domain which interacts with the bacterial cell wall or membrane, and
- c) an enzymatic antimicrobial peptidic domain from mammal's immune system;
- wherein
- a) the non-enzymatic antimicrobial peptidic domain from mammal's immune system is selected from the group consisting of: a defensin, a histatin, and a cathelicidin;
- b) the bacterial binding peptidic domain is selected from the group consisting of: a peptidic domain from a Pattern Recognition Receptor which binds to a Pathogen-Associated Molecular Pattern, and a bacteriophage adhesin; and
- c) the enzymatic antimicrobial peptidic domain from mammal's immune system is selected from the group consisting of: a secretory phospholipase, a lactoferrin, a transferrin, a lactotransferrin and lyzosyme.

Another aspect of the invention relates to inclusion bodies comprising a recombinant antimicrobial multidomain polypeptide herein provided in the other aspects.

In this description, the term "polypeptide" and "protein" are used interchangeably as synonymous. The term "peptidic domain" relates to a sequence of amino acid nature.

The term "recombinant" means that the polypeptide has been produced by the manipulation of a biological expression system such that expresses large amounts of a recombinant DNA molecule of interest.

The term "antimicrobial", as used herein, means that the polypeptides of the present invention inhibit, prevent, or destroy the growth or proliferation of microbes such as bacteria, fungi, viruses, parasites or the like. Antimicrobial can also be generally referred as disinfectant, antiseptic, or antibiotic.

In the field of antimicrobials it is not clear the distinction between the terms "Host Defense Peptides" (HDPs), and "Antimicrobial Peptides" (AMPs). Many times they are used interchangeably as synonymous. Both can be defined as small cationic amphiphilic peptides synthesized by nearly all multicellular organisms able to kill bacteria through the disruption of their basic cell wall structures. These positively charged peptides have bactericidal broadspectrum activity since their action is based on their interaction and further disruption of negatively charged bacterial cell envelope.

In relation to the polypeptide of the invention, it is understood in the present context that (a) a non-enzymatic antimicrobial peptidic domain from mammal's immune system belong to the category of HDPs or AMPs whereas (c) an enzymatic antimicrobial peptidic domain from mammal's immune system does not, being both (a) and (c) peptides (or enzymes) generated by a mammal's innate immune system in response to foreign/pathogenic bacteria. The peptidic domain (b) does not belong neither to the category of HDPs or AMPs nor to immune system enzymes, but to peptides that interact (bind) with structures of the bacterial cell wall or membrane, thus promoting the capture of the bacteria.

The skilled in the art would easily know how to verify that a given peptide meets the definition of being a non-enzymatic or an enzymatic antimicrobial peptidic domain from mammal's immune system, and a bacterial binding peptidic domain that interacts with the bacterial cell wall or membrane. Such functionalities are testable by well-established assays.

As a way of example, to verify whether a given peptide is an enzymatic antimicrobial peptidic domain from mammal's immune system, a search in e.g. the following databases can be carried out: in sequence databases such as GenBank, European Nucleotide Archive and DNA Data Bank of Japan; secondary databases such as UniProt, database of protein sequences grouping together Swiss-Prot, TrEMBL and Protein Information Resource, and other databases like Protein Data Bank, Ensembl and InterPro. After databases search, the output result will indicate the homology of the query sequence with a specific DNA sequence or protein and it will be possible to search for its function. Depending on this search it could be classified or not as enzymatic antimicrobial peptide. Moreover a colorimetric, fluorimetric or luminometric assay can be done using the substrate of the catalytic motif of the enzymatic antimicrobial peptidic domain to be tested.

Similarly, to verify whether a given peptide is an non-enzymatic antimicrobial peptidic domain from mammal's immune system, a search in in e.g. the following databases can be carried out: sequence databases such as GenBank, European Nucleotide Archive and DNA Data Bank of Japan; secondary databases such as UniProt, database of protein sequences grouping together Swiss-Prot, TrEMBL and Protein Information Resource, and other databases like Protein Data Bank, Ensembl and InterPro. After databases search, the output result will indicate the homology of the query sequence with a specific DNA sequence or protein and it will be possible to search for its function. Depending on this search it could be classified or not as a HDP or AMP. Moreover a general viable cell enumeration assay after the incubation of the non-enzymatic antimicrobial peptidic domain of interest with a bacterial strain can be done. The reduction of viable cell counts (CFU/ml) after the incubation with the peptide verifies that belongs to AMP category.

To verify whether a given peptide is a bacterial binding peptidic domain which interacts with the bacterial cell wall or membrane, an ELISA-based immunoassay can be done using the target bacteria as antigen and the specific binding peptidic domain of interest as tested biological reagent. The specific signal of recognition of recombinant antibody with target bacteria, either in colorimetric or fluorescence/luminescent signal in comparison to control samples (without recombinant antibody) indicates that the peptide of interest interacts with bacterial cell wall o membrane.

The working examples herein provided demonstrate on one hand, that the multidomain polypeptides have been satisfactorily expressed in IBs and in good amounts to be industrially viable. On the other hand, it is demonstrated that the polypeptides have a broadspectrum antimicrobial effect, attacking both Gram negative and Gram positive bacteria (in the Examples, *Enterococcus faecium* as example of Gram positive, and *Klebsiella* as Gram negative). It is noted that the bacterial strains used in the experimental examples are antibiotic resistant strains and the results demonstrate that the polypeptides of the invention are effective against them. These two points have been demonstrated using different polypeptide molecules following the structure of the at least three domains.

Furthermore, Examples 13 and 14 demonstrate that if e.g. defensin 5 (HD5) is combined with the other peptidic domains conforming the multidomain polypeptide of the invention, its activity is significantly higher than the activity of defensin 5 alone (as synthetic molecule or recombinantly produced). Thus, it is demonstrated that the combination of the three peptidic domains described herein in a single multidomain polypeptide has a higher antimicrobial effect than the individual domains, thereby plausibly demonstrating that the multidomain polypeptides herein provided have a significant synergistic antimicrobial effect in relation to the AMPs or peptidic domains separately used. These results are in line with the previous Examples demonstrating that the multidomain polypeptides have a significant broadspectrum antimicrobial effect.

Without being bound to the theory, it is believed that this is the first time that a recombinant polypeptide with antimicrobial properties in a multidomain form comprising at least three peptidic domains as explained before is obtained. As said before, previous attempts have been focused to produce an AMP with a carrier molecule (e.g. SUMO protein) in form of fusion protein, to avoid the problems of toxicity to the bacterial expression cells. In that sense, herein is provided a recombinant antimicrobial multidomain polypeptide with three AMP domains, wherein the polypeptide is no toxic for the bacterial expression cells but also, remarkably, being all domains functional (i.e. with antimicrobial function, not as "simple carriers" as SUMO protein).

Thus, based on the knowledge of the prior art, the skilled person could not have foreseen with a reasonable expectation of success that the herein described polypeptides would work with the significant effects as shown in the Examples and overcoming the above-mentioned drawbacks.

By the way of the invention, additional particular subproblems are solved at the same time, as demonstrated herein by the working Examples: an antimicrobial agent with a broad spectrum antimicrobial effect is provided and is produced in an efficient production system, i.e in form of IBs. This format is a protein-based nanocluster (also known as protein aggregate) that is generated during the recombinant production. One advantage of this protein format is the one-step production process. This means that, in contrast to the encapsulation of active biomolecules in nanocarriers, involving two separate processes (the production of the carriers and the biomolecule separately), the production of protein aggregates is achieved in one single step. Inclusion bodies are non-enveloped, porous, mechanically stable protein nanoclusters with sizes ranging from 50 to 500 nm in diameter generated in vivo, through a stereo-specific process during most of the recombinant protein production processes. The Examples related to antimicrobial assays clearly prove that the polypeptide embedded in such aggregates is properly folded and functional.

Other advantages achieved by the invention are that:

The polypeptide is stable with no need of adding excipients to stabilize the polypeptide, thereby simplifying the final formulation;

The dose to be administered is reduced;

A slow release of the embedded polypeptide is observed once the particles are administered, which is good for several applications;

If needed, it constitutes a source of purifyable soluble polypeptide since the IBs are mainly formed by the polypeptide of interest (i.e. it is used as a pre-enriched phase).

Further, the polypeptide of the invention in the form of IBs has demonstrated bacterial antibiofilm activity, thereby being useful for several uses, by direct application of the polypeptide of the invention to e.g. surfaces, medical devices or for topical use.

Moreover, the production of proteins in an aggregated format significantly reduces the production and purification costs, making it economically viable. Another aspect of the invention relates to a DNA construct comprising a sequence codifying for the antimicrobial multidomain polypeptide as defined herein.

The invention also provides methods and products for producing the recombinant antimicrobial multidomain polypeptides. Thus, an aspect of the invention is related to a process for the production of a recombinant antimicrobial multidomain polypeptide of the invention, which involves the expression of said polypeptide as a heterologous protein in bacterial expression cells, wherein the polypeptide is accumulated in IBs, the process comprising the steps of:

i) growing bacterial expression cells which comprise a DNA construct codifying for the antimicrobial multidomain polypeptide;

ii) inducing the expression of the DNA construct by a specific inducer and further incubating the bacterial cells;

iii) lysing the bacterial cells by means of a mechanical and/or enzymatic disruption method; and iv) purifying the IBs by washing with buffers and/or detergents.

Other aspects of the invention relate to the recombinant antimicrobial multidomain polypeptide or the inclusion bodies of the invention for use as antimicrobial agent, as antibiofilm agent and the use of the polypeptide for the disinfection of medical and surgical materials.

Another aspect relates to the recombinant antimicrobial multidomain polypeptide or the inclusion bodies of the invention, for use as a medicament, particularly, for use in the treatment and/or prevention of bacterial infections.

An aspect of the invention relates to a pharmaceutical or veterinary composition comprising the recombinant antimicrobial multidomain polypeptide or the inclusion bodies of the invention and a carrier, diluent or excipient.

An aspect of the invention relates to an item impregnated with, coated in or covered by a composition comprising a recombinant antimicrobial multidomain polypeptide or the inclusion bodies of the invention, wherein the item is selected from the group consisting of: a medical device, medical instrument, medical implement, prosthetic, implantable device or material, wound dressing and a biologically compatible material.

Finally, another aspect of the invention is a biologically compatible material selected from the group consisting of plastic, metal, cement, glue, composite, tissue scaffold and wound dressing incorporating or impregnated with a composition comprising the polypeptide or the inclusion bodies of the invention.

DETAILED DESCRIPTION OF THE INVENTION

Recombinant Antimicrobial Multidomain Polypeptide

Figure 1A:
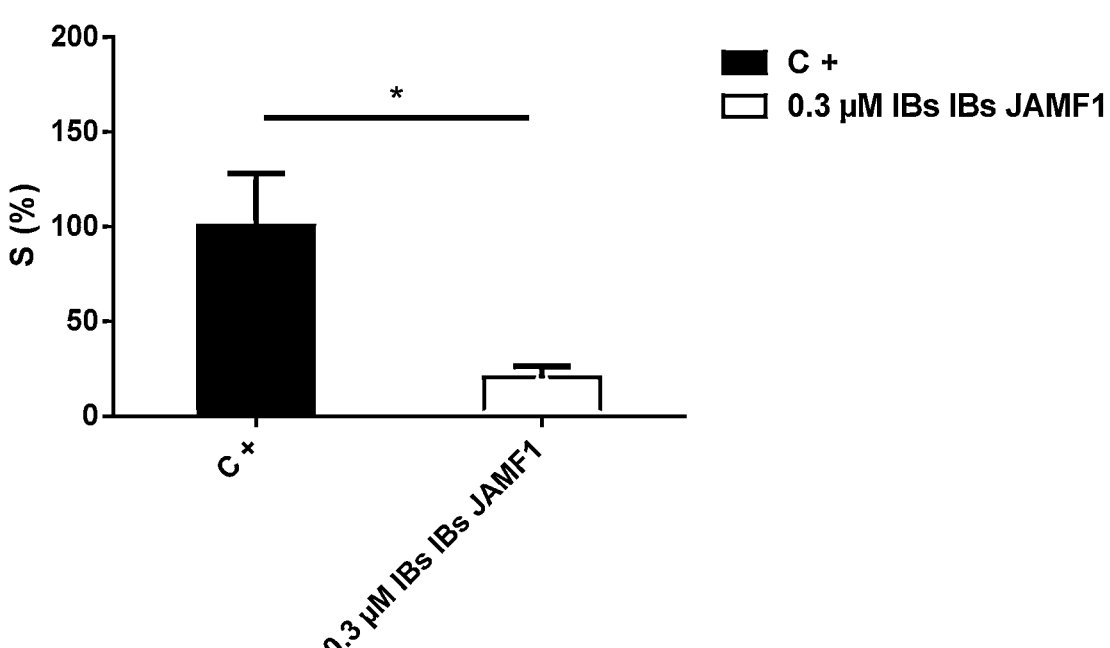
FIG. 1A Antibacterial activity assay and FIG. 1B Reporter enzymatic assay in the presence of JAMF1 IBs at 37° C. overnight (ON). S=Survival, C=Control, IBs=Inclusion bodies. *P <0.05. See working Examples 3 and 4 herein for further details.

In an embodiment, the recombinant antimicrobial multidomain polypeptide has bactericidal activity.

The recombinant antimicrobial multidomain polypeptide of the first aspect as discussed above comprises at least three peptidic domains independently selected each one from the three above-mentioned domains (a), (b), and (c). That means that the polypeptide can be constituted by at least three domains, each one belonging to a different category between (a), (b) and (c) or belonging to the same category; e.g. having three domains (a)-(a)-(a) or (a)-(b)-(b). The polypeptide can also comprise more than three domains.

In a particular embodiment, the polypeptide comprises three peptidic domains, wherein one domain is (a) a non-enzymatic antimicrobial peptidic domain from mammal's immune system, another domain is (b) a bacterial binding peptidic domain which interacts with the bacterial cell wall or membrane, and the other one is (c) an enzymatic antimicrobial peptidic domain from mammal's immune system. In a particular embodiment, the peptidic domains (a), (b) and (c) are different from each other; that is the polypeptide is comprised by at least three structurally different domains (i.e. different molecules), each one selected from one property (a), (b) or (c). Besides this selected property, each domain can have an additional property (a), (b) or (c).

In an aspect, the recombinant antimicrobial multidomain polypeptide comprises at least three peptidic domains:

a) a non-enzymatic antimicrobial peptidic domain from mammal's immune system, b) a bacterial binding peptidic domain which interacts with the bacterial cell wall or membrane, and c) an enzymatic antimicrobial peptidic domain from mammal's immune system;

wherein a) the non-enzymatic antimicrobial peptidic domain from mammal's immune system is selected from the group consisting of: a defensin, a histatin, and a cathelicidin;

b) the bacterial binding peptidic domain is selected from the group consisting of: a peptidic domain from a Pattern Recognition Receptor which binds to a Pathogen-Associated Molecular Pattern, and a bacteriophage adhesin; and c) the enzymatic antimicrobial peptidic domain from mammal's immune system is selected from the group consisting of: a secretory phospholipase, a lactoferrin, a transferrin, a lactotransferrin and lyzosyme.

Thus, the peptidic domains (a), (b), (c) are structurally different from each other.

In a particular embodiment, a) the non-enzymatic antimicrobial peptidic domain from mammal's immune system is a defensin;

b) the bacterial binding peptidic domain is a peptidic domain from a Pattern Recognition Receptor which binds to a Pathogen-Associated Molecular Pattern; and c) the enzymatic antimicrobial peptidic domain is secretory phospholipase.

(a) Non-Enzymatic Antimicrobial Peptidic Domain from Mammal's Immune System

In a particular embodiment the non-enzymatic antimicrobial peptidic domain from mammal's immune system is selected from the group consisting of: a defensin, a histatin, and a cathelicidin.

These three types of antimicrobial peptides from mammal's immune system are described in Smet 2005, which is herein incorporated by reference. Defensins is a family of cationic non-glycosylated peptides containing six cysteine residues that form three intramolecular disulphide bridges, resulting in a triple-stranded beta-sheet structure. They have molecular masses of 3.5-6 kDa. In humans for example, two classes of defensins can be found: alfa-defensins and beta-defensins. In humans, four alfa-defensins have been isolated from neutrophils (HNP1 to 4). All four alfa-defensins can be found in the azurophilic granules of neutrophil granulocytes. HNP1 to 3 are also found in B cells and natural killer cells. In neutrophils, the alfa-defensins play a role in the oxygen-independent killing of phagocytosed microorganisms. Two alfa-defensins (HD-5 and 6) are referred to as enteric defensins, and are found in the granules of Paneth cells of the small intestine and in the epithelial cells of the female urogenital tract. Examples of human beta-defensin are HBD1, expressed in epithelia that are directly exposed to the environment or microbial flora (e.g. in the lung, mammary gland, salivary gland, kidney, pancreas and prostate); HBD2, widely expressed in epithelia (lung, gut, urogenital system, pancreas and skin), leukocytes and the bone marrow; and HBD3, mainly expressed in skin and tonsils. Bovine lingual antimicrobial peptide (LAP) is also a member of the beta-defensin family in cows.

The defensin-related HE2 isoforms (human epidilymis 2) is a family of small cationic secretory peptides of 4-8 kDa that derive from the multiple mRNAs generated from HE-2 gene. HE-2alfa and HE-2beta1 are the most prevalent isoforms.

Histatins is a group of small, cationic, histidine-rich peptides of 3-4 kDa present in human saliva. Histatins adopt a random coil conformation in aqueous solvents and form alfa-helices in non-aqueous solvents. The histatin family consists of several members, of which histatin 1, 3 and 5 are the most important. Histatins are encoded by two closely related genes (HIS1 and HIS2), with histatin 1 and histatin 3 as primary products of HIS1 and HIS2, respectively. Histatin 5 is formed by further processing of histatin 3. P-113, a 12-amino-acid fragment of histatin 5 retains antimicrobial activity.

The third group within (a) non-enzymatic antimicrobial peptidic domain from mammal's immune system are cathelicidins which are HDPs synthesized and stored in circulating leukocytes and numerous types of epithelial tissues in particular the gastrointestinal tract and skin. The most known example is the cathelicidin LL-37. Indolicin (cathelicidin-4) also belongs to this category. This peptide is derived proteolytically from the C-terminal end of the human CAP18 protein. Just like the histatins, it adopts a largely random coil conformation in a hydrophilic environment, and forms an alfa-helical structure in a hydrophobic environment.

Thus, in particular embodiments, the non-enzymatic antimicrobial peptidic domain from mammal's immune system is one selected from the above-mentioned. More particularly, it is a defensin. In a more particular embodiment, it is an alfa-defensin; and more particularly the alfa-defensin is selected from the group consisting of HNP-1, HNP-2, HNP3, HNP4, HD5 and HD-6. In another particular embodiment, it is a beta-defensin; and more particularly the beta-defensin is selected from the group consisting HBD-1, HBD-2, HBD-3, HBD-4 and bovine lingual antimicrobial peptide (LAP). In another embodiment, the peptidic domain is a defensin-related HE2. In another embodiment, the peptidic domain is a histatin, and more particularly the histatin is selected from the group consisting of: Hst1, Hst3, Hst5 and P113. In another embodiment, the peptidic domain is the cathelicidin LL-37 or indolicin.

In even a more particular embodiment, the non-enzymatic antimicrobial peptidic domain from mammal's immune system is human alfa-defensin 5 (HD-5). In another particular embodiment the non-enzymatic antimicrobial peptidic domain from mammal's immune system is the fragment from amino acid 63 to 94 from HD-5.

(b) Bacterial Binding Peptidic Domain which Interacts with the Bacterial Cell Wall or Membrane Binding domain or bacterial capture domain refers to host (mammals) immune constituents. The mode of action of this peptidic domain with bacterial binding capacity is immobilizing the bacteria to be killed in the antimicrobial action zone, by interacting with essential cellwall or cell-membrane components. In a particular embodiment, the bacterial binding peptidic domain is selected from the group consisting of: a peptidic domain from a Pattern Recognition Receptor (PRR) which binds to a Pathogen-Associated Molecular Pattern (PAMP), and a bacteriophage adhesin, which is capable of recognizing specific receptors on the bacterial surface such as T4 phage adhesins gp37 or gp12 binding to *Escherichia coli* lipopolysaccharide (LPS) or T2 phage adhesin gp38 which also binds to *Escherichia coli* LPS.

PRRs from immune system recognize conserved structures common to a broad variety of microorganisms. These target structures are called PAMPs and microbial proteins. In a particular embodiment, the peptidic domain from a PRR is selected from the group consisting of: a Toll Like receptor, a scavenger receptor, a mannose receptor, a plasma gelsolin and a C-lectin.

In a more particular embodiment, the bacterial binding peptidic domain is gelsolin, which is able to bind both lipopolysaccharide (LPS) from Gram-negative bacteria and lipoteichoic acid (LTA) from Gram-positive bacteria. In another particular embodiment the bacterial binding peptidic domain is the fragment from amino acid 188 to 196 from gelsolin.

(c) Enzymatic Antimicrobial Peptidic Domain from Mammal's Immune System

This antimicrobial peptidic domain is one involved in host defense able to kill bacteria through an enzymatic degradation of their membrane and wall. In an embodiment, the enzymatic antimicrobial peptidic domain from mammal's immune system is selected from the group consisting of: a secretory phospholipase (sPLA), a lactoferrin, a transferrin, a lactotransferrin, and lysozyme. Lactoferrin and transferrin found in body secretions, plasma, and tissue fluid, trap iron for use by human cells while preventing its use by microorganisms.

Within the group of sPLAs, there are different categories. Currently, at least 11 mammalian isoforms of sPLA2 are identified and belong to Group I, II, III, V, IX, X and XII. Of these, Groups I, II, V and X are considered "conventional" sPLA2. They share a variety of structural elements including a His/Asp catalytic dyad, a highly conserved $Ca^{2+}$ binding domain and six absolutely conserved disulfide bonds. Groups III and XII, on the other hand, are structurally distinct based on the identity of their protein sequence with Groups I, II, V and X sPLA2. They only share the aforementioned groups in their $Ca^{2+}$ binding loop and catalytic site.

In a more particular embodiment, the enzymatic antimicrobial peptidic domain is sPLA2 (included in group XIIA of sPLAs), which is an enzyme that penetrates the bacterial cell wall and hydrolyzes the phospholipids in the bacterial cytoplasmic membrane. In another particular embodiment the enzymatic antimicrobial peptidic domain is the fragment from amino acid 23 to 189 from sPLA2.

Fragments of all the above-mentioned peptides (i.e. from domains a, b and c) that retain their original antimicrobial activity (e.g. the catalytic domain in the case of enzymes) are also encompassed by the present invention.

In a particular embodiment, a) the non-enzymatic antimicrobial peptidic domain from mammal's immune system is a human defensin 5;

b) the bacterial binding peptidic domain is gelsolin; and c) the enzymatic antimicrobial peptidic domain is secretory phospholipase A2.

Aggregation Tags, Purification Tags and Linkers

In a particular embodiment, the recombinant antimicrobial multidomain polypeptide further comprises at least one aggregation tag or also called "pull-down" tag, which enhance the formation of IBs. Further, the inventors have seen that the inclusion of aggregation tags in the polypeptide surprisingly reduces the toxicity caused by the polypeptide to the bacterial expression cells, as it is demonstrated in the Example 15.

In a particular embodiment, the aggregation tag is located at N-terminal end or at C-terminal end of the polypeptide.

In another particular embodiment, one aggregation tag is located at N-terminal end and one aggregation tag is located at C-terminal end of the polypeptide, thereby flanking the polypeptide.

Examples of aggregation tags are GFIL8 (GFILGFIL, SEQ ID NO: 12), GFIL16 (GFILGFILGFILGFIL, SEQ ID NO: 13), alpha helical peptide 18A (EW-LKAFYEKVLEKLKELF, SEQ ID NO: 14), beta-strand peptide ELK16 (LELELKLKLELELKLK, SEQ ID NO: 15), surfactant-like peptide $L_6KD$ (LLLLLLKD, SEQ ID NO: 16), $L_6K_2$ (LLLLLLKK, SEQ ID NO: 17), DKL6 (DKLLLLLL, SEQ ID NO: 18), the 42-mer Alzheimer's amyloid peptide Aβ42 (F19D), VP1 protein from foot-and-mouth disease virus, coiled-coil domain (53 amino acids) TDoT of the cell-surface protein tetrabrachion, and CBD-Clos (cellulose-binding domain from *Clostridium cellulovorans*).

In a more particular embodiment, the recombinant antimicrobial multidomain polypeptide comprises two aggregation tags which are complementary domains, one tag being located at N-terminal end and the other tag being located at C-terminal end, thereby flanking the polypeptide. Examples of aggregation tags of this type are antiparallel leucine zipper domains, which are two-stranded α-helical heterodimers, more particularly jun-fos pair; particularly fos leucine zipper (118-210 amino acids) and jun leucine zipper (257-318 amino acids) are used. Another example is Src homology 3 (SH3) and Src homology 2 (SH2) domains that mediate protein interactions. Particularly, the aggregation tags are a jun-fos pair.

In a particular embodiment, the recombinant antimicrobial multidomain polypeptide comprises at least a purification tag to facilitate protein purification. This tag is normally located at C-ter or N-ter and after the aggregation tags if present. In a particular embodiment, the purification tag is a 6 Histidine tag (H6).

In a particular embodiment, the peptidic domains are linked with peptidic linkers, which are short peptide sequences that occur between protein domains. In a particular embodiment, linkers are often composed of flexible residues like glycine and serine so that the adjacent protein domains are free to move relative to one another. Linkers are used to ensure that two adjacent domains do not sterically interfere with one another. Particularly, linkers are flexible and generally with a length between 2 and 20 amino acids.

In a particular embodiment, the recombinant antimicrobial multidomain polypeptide comprises the amino acid sequence SEQ ID NO: 10, identified in this description as JAMF1. In another embodiment, the antimicrobial multidomain polypeptide comprises the amino acid sequence SEQ ID NO: 11, identified in this description as JAMF2. See Example 1 for more details of the two constructions JAMF1 and JAMF2.

Minor modifications of the primary amino acid sequence of the polypeptide of the invention may result in polypeptides that have substantially equivalent activity as compared to the specific polypeptides described herein. Sequence variation may be caused by the use of e.g. different sequences of a given peptidic domain that can vary between species or e.g. different isoforms of a given peptidic domain.

In a particular embodiment, the recombinant antimicrobial multidomain polypeptide comprises an amino acid sequence which has at least a 70% identity to the sequence SEQ ID NO: 10. Another embodiment of the invention is related to a recombinant antimicrobial multidomain polypeptide comprising an amino acid sequence which has at least a 70% identity to the sequence SEQ ID NO: 11. More particularly, the % of identity in respect of SEQ ID NO: 10 and 11 is at least 75%, 80%, 85%, 90% or 95%. The term "% identity" is well understood in the art as the amount of characters which match exactly between two different sequences. All of the polypeptides produced by these modifications are included herein as long as the antimicrobial activity of the original polypeptide still exists. The activities are testable as discussed above.

Process for the Production of the Recombinant Antimicrobial Multidomain Polypeptide As said before another aspect of the invention is related to a process for the production of the recombinant antimicrobial multidomain polypeptide, which involves the expression of said polypeptide as a heterologous protein in bacterial expression cells, wherein the polypeptide is accumulated in IBs. The process comprises the steps of: i) growing bacterial expression cells which comprise a DNA construct codifying for the antimicrobial multidomain polypeptide; ii) inducing the expression of the DNA construct by a specific inducer and further incubating the bacterial cells; iii) lysing the bacterial cells by means of a mechanical and/or enzymatic disruption method; and iv) purifying the IBs by washing with buffers and/or detergents.

There are many bacterial expression cells which are suitable for the purpose of the invention. In particular embodiments, the bacterial expression cells are cells of *E. coli* (e.g. *E. coli* DE3 strain), or GRAS species—Generally Recognized As Safe—for not having endotoxins such as *Lactococcus lactis, Lactobacillus plantarum* or *Corynebacterium glutamicum* strains.

Particularly, the expression cells are first grown at their optimal temperature (i.e. between 3° and 37° C.) in a culture medium and when a certain biomass is achieved, expression of the heterologous DNA sequence is induced by a specific inducer, particularly isopropyl-β-d-thiogalactoside (IPTG), nisin, temperature or other specific peptides. Cells are further incubated at a temperature between 25 and 42° C. and during 3 h to 16 h.

The mechanical and/or enzymatic disruption methods are known by the skilled in the art. Examples of enzymatic disruption methods include incubation with protease inhibitors, phenylmethanesulphonylfluoride (PMSF) and lysozyme. Mechanical methods include sonication, cell disruptors or french press and freezing cycles. The step of purifying the IBs by washing with buffers and/or detergents is also well known by the skilled in the art. In a particular embodiment, the IBs are incubated for example in Triton X-100, Nonidet P40 (NP40), MgSO₄, Tris-HCl, NaCl and EDTA.

The IBs containing the recombinant antimicrobial multidomain polypeptide can be directly used (see below). Furthermore, for applications with the soluble polypeptide, IBs constitute a pre-enriched phase for obtaining soluble polypeptide. To this end, in a particular embodiment the process for the production of the recombinant antimicrobial multidomain polypeptide further comprises: v) solubilizing the IBs to obtain the soluble polypeptide in mild conditions with detergent and/or buffers incubations; and vi) separating the soluble polypeptide by chromatography.

An aspect of the invention relates to the soluble recombinant antimicrobial multidomain polypeptide obtainable by the process of solubilization described above.

The step of solubilizing the IBs to obtain the soluble polypeptide in mild conditions with detergent and/or buffers incubations is well known by the skilled in the art. In a particular embodiment, the IBs are incubated for example in 0.2% N-lauroyl sarcosine. In particular, an affinity chromatography is used but other techniques are also suitable, as e.g. sizeexclusion chromatography or ionic chromatography.

In a particular embodiment, when the multidomain polypeptide comprises aggregation and/or purification tags, the process further comprises an additional step of removing the aggregation and/or purification tags by using specific proteases.

In order to express the recombinant antimicrobial multidomain polypeptide, bacterial expression cells comprise a DNA construct codifying for the antimicrobial multidomain polypeptide. Said DNA construct comprises at least three DNA sequences codifying for three peptidic domains, wherein each peptidic domain is selected from the group consisting of: (a) a non-enzymatic antimicrobial peptidic domain from mammal's immune system, (b) a bacterial binding peptidic domain which interacts with the bacterial cell wall or membrane, and (c) an enzymatic antimicrobial peptidic domain from mammal's immune system.

In particular embodiments, the DNA construct further comprises a DNA sequence codifying for at least an aggregation tag and/or a DNA sequence codifying for at least a purification tag and/or DNA sequences codifying for a linker.

In other embodiments, the DNA construct further comprises protease cleavage sites to remove the aggregation and/or purification tags.

Applications of the Recombinant Antimicrobial Multidomain Polypeptide or the Inclusion Bodies Comprising it as Antimicrobial and Antibiofilm Agent, and in the Disinfection of Medical and Surgical Devices As discussed above, an aspect of the invention is the polypeptide or the inclusion bodies comprising it for use as antimicrobial agent. Another aspect of the invention is polypeptide or the inclusion bodies comprising it for use as antibiofilm agent.

In a particular embodiment, the polypeptide or the inclusion bodies comprising are used in food preservation. Because of the antimicrobial properties of the polypeptide and the inclusion bodies, they may also be used as preservative or sterillant of materials susceptible to microbial contamination. The polypeptide and the inclusion bodies of the invention can be used as broad-spectrum antimicrobial agent directed toward various specific applications. Such applications include use of the polypeptides and inclusion bodies as preservatives in processed foods (organisms including *Salmonella, Yersinia*, and *Shigella*), either alone or in combination with antibacterial food additives such as lysozymes; as a topical agent (*Pseudomonas, Streptococcus*) and to kill odor-producing microbes (Micrococci).

A particular embodiment of said aspects is the use of the polypeptide or the inclusion bodies in the disinfection of medical and surgical materials, i.e. to protect medical material from colonization with pathogens and avoid and/or treat biofilm formation. Thus, the polypeptide or the inclusion bodies of the invention can be used as material coating (medical and surgical devices) and for surface cleaning and sterilization (in the form of detergents, or disinfectants). Remarkably, the polypeptide in the form of IBs can be directly applied for such applications, as it is shown in the Examples provided herein (Example 6). The polypeptide is effective and is slow-released.

As discussed, an aspect of the invention is an item impregnated with, coated in or covered by a composition comprising the polypeptide or the inclusion bodies, wherein the item is selected from the group consisting of: a medical device, medical instrument, medical implement, prosthetic, implantable device or material and wound dressing.

Another aspect of the invention is a biologically compatible material selected from the group consisting of plastic, metal, cement, glue, composite, tissue scaffold and wound dressing incorporating or impregnated with a composition comprising the polypeptide or the inclusion bodies of the invention.

In all the applications, the polypeptide can be used directly in the form of IBs or in the form of soluble polypeptide.

Medical Applications of the Recombinant Antimicrobial Multidomain Polypeptide or the Inclusion Bodies Comprising it As discussed, an aspect of the invention is the polypeptide or the inclusion bodies for use as a medicament. Particularly, the polypeptide or the inclusion bodies are used in the treatment and/or prevention of bacterial infections. This aspect can be alternatively formulated as the use of the polypeptide or the inclusion bodies as defined herein for the manufacture of a pharmaceutical product, a medicament or a veterinary product, for the prevention and/or treatment of bacterial infections. This may be also alternatively formulated as a method for the prevention and/or treatment of an bacterial infections in a mammal, including a human, comprising administering to said mammal in need thereof an effective amount of the polypeptide or the inclusion bodies as defined herein. Bacteria causing infection are particularly Eubacteria, including Gram negative and Gram positive bacteria.

In particular, the polypeptide or the inclusion bodies are used as antimicrobial and antibiofilm agent for topical treatment (wound healing, epithelial infection, etc). Remarkably, the polypeptide in the form of IBs can be directly applied for such applications without the need of solubilization of the IBs and without the need of adding stabilizing excipients for the topical administration.

In all medical applications, the polypeptide can be used directly in the form of IBs or in the form of soluble polypeptide.

Pharmaceutical and Veterinary Compositions

As discussed above, the invention also provides a pharmaceutical or veterinary composition comprising the polypeptide or the inclusion bodies, and an acceptable carrier, diluent or excipient. Particularly, the pharmaceutical or veterinary composition is for topical administration.

As used herein "acceptable carrier" includes any and all solvents, dispersion media, coatings, antibacterial and antifungal agents, isotonic and absorption delaying agents, and the like that are physiologically compatible. In one aspect, the carrier is suitable for parenteral administration. Alternatively, the carrier can be suitable for intravenous, intraperitoneal or intramuscular administration. In another aspect, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is compatible with the active compound, use thereof in the pharmaceutical compositions is contemplated. Supplementary active compounds can also be incorporated into the compositions.

In prophylactic applications, pharmaceutical/veterinary compositions are administered to a patient susceptible to, or otherwise at risk of a disease or condition (i.e., as a result of bacteria, fungi, viruses, parasites or the like) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicaments are administered to a patient suspected of, or already suffering from such a disease or condition in an amount sufficient to cure, or at least partially arrest, the symptoms of the disease or condition (e.g., biochemical and/or histologic), including its complications and intermediate pathological phenotypes in development of the disease or condition. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved.

Pharmaceutical/veterinary compositions of the invention also can be administered in combination therapy, i.e., combined with other agents. For example, in treatment of bacteria, the combination therapy can include a composition of the present invention with at least one agent or other conventional therapy.

Unless otherwise defined, all technical and scientific terms used herein have the same meaning as commonly understood by a person skilled in the art. Methods and materials similar or equivalent to those described herein can be used in the practice of the present invention. Throughout the description and claims the word "comprise" and its variations such as "comprising" are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein. The following examples and drawings are provided herein for illustrative purposes, and without intending to be limiting to the present invention.

EXAMPLES

Example 1: Antimicrobial Multidomain Polypeptide Design

Two antimicrobial constructs were designed and synthesized. From N-terminal to C-terminal, the gene for the JAMF1 construct consists of the sequences encoding Jun257-318 (Uniprot entry P05412), Human Defensin-5 precursor (Uniprot entry Q01523), Gelsolin188-196 (Uniprot entry P06396), Group-XIIA secretory phospholipase A2 (sPLA2) precursor (Uniprot entry Q9BZM1), Fos118-210 (Uniprot entry P01100). Additionally, a linker sequence encoding SGGGSGGS (SEQ ID NO: 1) is used to connect between each of the domains. The second construct, JAMF2 is identical to JAMF1 but contains a modified form of both Human Defensin-5 (aminoacids 63-94) and Group-XIIA sPLA2 (aminoacids 23-189). All constructs feature a C-terminal H6-Tag to facilitate protein purification. Each fusion construct was cloned into pET22b (AmpR) (Novagene) vector using NdeI and XhoI restriction enzymes, at 5' and 3', respectively. The DNA sequences of all the genetic constructs were codon optimized by GeneArt (Regensburg, Germany) for its expression in *E. coli* BL21 (DE3).

JAMF1: Fos-linker-Human defensin 5-linker-Gelsolin-linker-Phospholipase-linker-Jun-H6

JAMF2: Fos-linker-Human defensin 5*-linker-Gelsolin-linker-Phospholipase*-linkerJun-H6

*modified sequence

TABLE 1

Design of the antimicrobial multidomain polypeptide

| Domain (N-ter to C-ter order) | Activity/Function |
|---|---|
| Fos leucine zipper (118-210 amino acids) | Control particle aggregation |
| Human defensin 5 | Non-enzymatic antimicrobial activity |
| Gelsolin | Bacterial binding (capture) |
| Phospholipase | Enzymatic antimicrobial activity |
| Jun Leucine Zipper (257-318 amino acids) | Control particle aggregation |
| H6 | Purification tag |

TABLE 2

Polypeptide sequences

| Protein construct | Amino acid sequence |
|---|---|
| JAMF1 (SEQ ID NO: 10) | (SEQ ID NO: 2)-(SEQ ID NO: 1)-(SEQ ID NO: 3)-(SEQ ID NO: 1)-(SEQ ID NO: 4)-(SEQ ID NO: 1)-(SEQ ID NO: 5)-(SEQ ID NO: 1)-(SEQ ID NO: 6)-(SEQ ID NO: 7) |
| JAMF2 (SEQ ID NO: 11) | (SEQ ID NO: 2)-(SEQ ID NO: 1)-(SEQ ID NO: 8)-(SEQ ID NO: 1)-(SEQ ID NO: 4)-(SEQ ID NO: 1)-(SEQ ID NO: 9)-(SEQ ID NO: 1)-(SEQ ID NO: 6)-(SEQ ID NO: 7) |

Example 2: Polypeptide Production

Protein Production:

*E. coli* BL21 (DE3) pET22b-JAMF1, *E. coli* BL21 (DE3)/pET22b-JAMF2 cultures were inoculated at an initial optical density at 600 nm ($OD_{600}$) of 0.05. Each culture was grown at 37° C. and 250 rpm in LB broth with 100 µg/ml of ampicillin to prevent plasmid loss. Protein expression was induced by 1 mM isopropyl-β-d-thiogalactoside (IPTG) when the $OD_{600}$ was 0.4-0.6. Cultures were grown 3 h post-induction.

Inclusion Body Purification:

Bacterial cultures were processed through a combination of mechanical and enzymatic disruption methods. Protease inhibitors (Complete EDTA-free, Roche), and phenylmethanesulphonylfluoride (PMSF) and lysozyme were added to the culture at a final concentration of 0.4 mM (Sigma-Aldrich) and 1 µg/ml (Sigma-Aldrich), respectively. After 2 h of incubation at 37° C. and 250 rpms the culture was centrifuged and resuspended in 50 ml of PBS supplemented with protease inhibitors (Complete EDTA-free, Roche). Then, the mixture was ice-jacketed and sonicated for 4 cycles of 1.5 minutes at 10% amplitude under 0.5 s cycles. After sonication, the mixture was frozen overnight (ON) at −80° C. The mixture was thawed and Triton X-100 was added (0.4% (v/v)) and incubated for 1 h at room temperature (RT). After this treatment, the mixture was frozen at −80° C. for 2 h and then thawed between for several cycles until no viable bacterial growth was detected. After that, 125

µl of Nonidet P40 (NP-40) was added and incubated for 1 hour at 4° C. Then, DNA was removed with DNAse at a final concentration of 0.6 µg/ml and $MgSO_4$ 0.6 mM for 1 h at 37° C. and 250 rpm. Samples were centrifuged at 15,000 g for 15 minutes at 4° C. The pellet containing IBs was washed with 25 ml lysis buffer (50 mM Tris-HCl PH 8, 100 mM NaCl, 1 mM EDTA and Triton X-100 0.5% (v/v)). Finally, a final centrifugation at 4° C. for 15 min and 15,000 g, pellets were stored at −80° C. until analysis. The IBs were quantified by western blot using a monoclonal anti-His antibody (His-probe, Santa Cruz). All incubations were done under agitation.

JAMF1 and JAMF2 IB Solubilization:

2 l of JAMF1 and 2 l of JAMF2 were produced in *E. coli* BL21 (DE3). Inductions were conducted for 3 h. The whole volumes were centrifuged at 6,000 g and the pellets were resuspended in 120 ml of PBS 1× in presence of protease inhibitors. Samples were subjected to 4 rounds of sonication for 5 minutes at 10% amplitude under 0.5 s cycle, intercalated by a minimum of 5 min repose in ice. Protein pellets were recovered and washed twice with distilled water. Pellets were weighted and solubilized in 0.2% N-lauroyl sarcosine and 40 mM Tris at a ratio of 40 ml/g of wet pellet as described by Peternel et al. 2008 and adding protease inhibitors. The mixture was incubated 40 h ON at RT under agitation and the supernatant was recovered through centrifugation at 15,000×g for 45 min at 4° C. for further purification.

Purification of the Solubilized JAMF1 and JAMF2:

NaCl and imidazole were added to the solubilized proteins to equilibrate the samples with the binding buffer composition, and Immobilized metal affinity chromatography (IMAC) purification was carried in an ÄKTA purifier FPLC (GE Healthcare) using 1 ml HisTrap HP columns (GE Healthcare). Both the binding and the elution buffer contained 0.2% N-lauroyl sarcosine, and the final imidazole concentration in the elution buffer was 0.5 mM. The buffer of the selected fractions was changed to KPi (potassium phosphate buffer: 80.2% v/v $K_2HPO_4$ and 19.8% v/v $KH_2PO_4$) using a desalting column (GE Healthcare). The amount of purified protein was determined by Bradford's assay, and the integrity of the protein analyzed by SDS-PAGE.

Aiming to evaluate the activity of JAMF1, the antimicrobial activity of JAMF1 as IBs (EXAMPLE 3) was determined as well as a fast reporter activity given by enzymatic domain (EXAMPLE 4).

Example 3: Antimicrobial Activity of JAMF1 as IBs

*E. coli* DH5a cultures were grown at 37° C. in LB broth until the $OD_{600}$ was 0.4-0.6 and subsequently diluted to obtain 10 million colony-forming units (CFU) per ml in 10 mM sterile KPi buffer. 100 µl from this suspension ($10^6$ CFUs) were centrifuged and the supernatant was removed. After that, either 100 µl of KPi buffer (Control) or 100 µl of KPi buffer containing JAMF1 at different concentrations were added. Then, bacterial cultures were incubated for 3 h or 16 h ON at 37° C. The cultures were then serially diluted using KPi buffer and plated in LB-agar dishes. After a 16 h incubation at 37° C., individual colonies of bacteria were counted manually. For each concentration of antimicrobial protein, the ratio of colonies counted to the number of colonies present on the control plate (0 µM) was calculated. Each condition was tested by triplicate and expressed as the average percentage of viable cells compared to the control.

Results and conclusions: FIG. 1A shows the antibacterial activity of JAMF1 multidomain protein produced as IBs. It is observed that JAMF1 IBs were active and reduced the *E. coli* survival up to 80%. These results prove the potential of the new generation of antimicrobial polypeptides based on multifunctional domains in an aggregated (IBs) format.

Example 4: Reporter Enzymatic Assay with JAMF1 in IBs

A fluorometric assay kit was used to measure sPLA2 activity (Cayman, Ann Arbor, MI, USA). Briefly, a PLA2 substrate consisting of 1,2-dithio analog of diheptanoyl phosphatidylcholine was used. Upon enzymatic hydrolysis of the thioester bond at the sn-2 position, free thiols were detected using 5,5'-dithio-bis-(2-nitrobenzoic acid) (DTNB) at 415 nm. Absorbance measurements were taken each 10 minutes ON. From the absorbance change per minute of the linear portion of the curve the reaction rate ($\mu$mol/min/ml) can be determined using the DTNB extinction coefficient. At least 8 time points were used for the calculations.

Figure 1B:
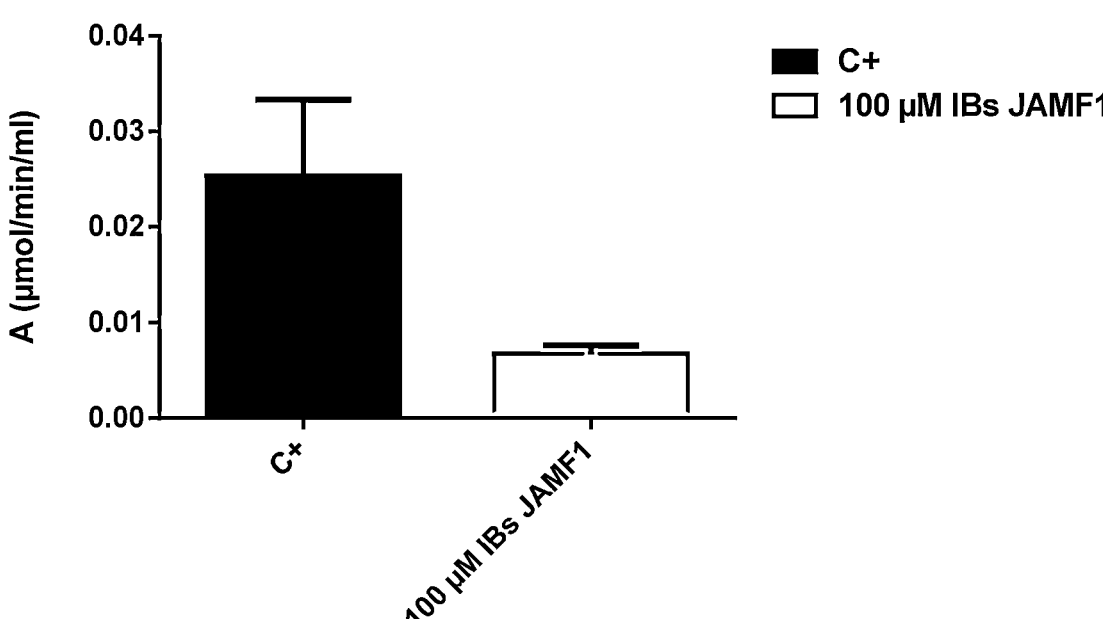

Results and conclusions: This assay shows (FIG. 1B) that JAMF1 IBs had enzymatic activity in at least one the fractions (soluble/IBs) tested. In the case of JAMF1, the soluble version had an activity even higher than the control used in this assay. This assay is a fast system to determine the activity of the enzymatic domain of the multidomain polypeptides of the invention, becoming a good reporter assay.

Example 5: Antimicrobial Activity of JAMF1 Using Different Pathogenic Strains to Evaluate its Broad-Spectrum Potential In a second step, the antimicrobial activity of JAMF1 was determined using different pathogenic strains to evaluate its broad-spectrum potential. For that, JAMF1 IBs were used.

*Klebsiella pneumoniae* Carbapenem resistant (KPC), *Klebsiella pneumoniae* Quinolone resistant (qnrA) and *Enterococcus* 204 *faecium* strains were grown at 37° C. in their corresponding growing medium until the $OD_{600}$ was 0.4-0.6 and subsequently diluted to obtain 10 million colony-forming units (CFU) per ml in sterile KPi buffer. 100 $\mu$l from this dilution ($10^6$ CFUs) were centrifuged at 6000×g for 15 min at 4° C. and the supernatant was removed. After that, either 100 $\mu$l of KPi buffer (Control) or 100 $\mu$l of KPi buffer containing antimicrobial protein at a concentration of 300 nM were added. Then, bacterial cultures were incubated for 16 h at 37° C. Then cultures were then serially diluted using KPi buffer and plated in LB-agar dishes. After a 16 h incubation at 37° C., individual colonies of bacteria were counted manually. For each strain, the ratio of colonies counted to the number of colonies present on the control plate (0 $\mu$M) was calculated. Each condition was tested by triplicate and expressed as the average percentage of viable cells compared to the control.

Figure 2:
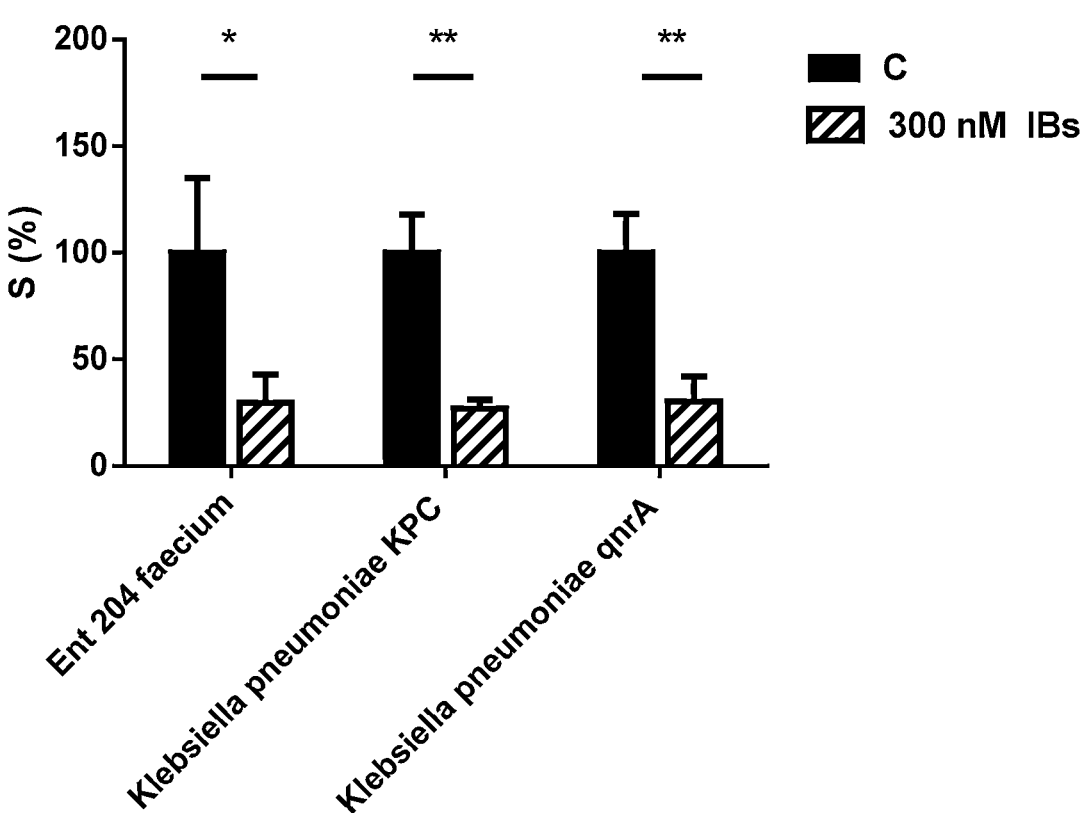
FIG. 2. Antibacterial activity assay: Survival of different pathogenic strains in presence of JAMF1 IBs at 37° C. ON. S=Survival, C=Control. Bacterial species on the x axis. *P<0.1 (tendency), **P<0.05. See working Example 5 herein for further details.

Results and conclusions: This study shows (FIG. 2) the antimicrobial activity of JAMF1 IBs with different pathogenic strains observing an inhibition of 70.2% E. 204 *faecium,* 73.2% *K. pneumoniae* KPC, and 74.5% for % *K. pneumoniae* qnrA. FIG. 2 shows that JAMF1 is a multidomain protein produced as IBs with anti-bacterial broad-spectrum activity against antibiotic-resistant strains.

Example 6: Antimicrobial Activity of JAMF1 IBs Immobilized in a Surface

In this study, the antimicrobial activity of JAMF1 IBs immobilized in a surface was evaluated, aiming to determine a wider range of possible applications of this new generation of antimicrobials.

*Klebsiella pneumoniae* Carbapenem resistant (KPC) was used as model strain. Briefly, an ON culture of the strains was grown at 37° C. and 250 rpm in its appropriate growth medium. Before the addition of bacteria for biofilm formation into a 24-well sterile plate, 80 $\mu$l of JAMF1 IBs at a concentration of 180 UM were added to each well and washed 3 times with sterile KPi buffer. After that, bacteria were diluted 1:200 in their corresponding medium supplemented with 0.2% (w/v) glucose, in 24-well sterile plates (400 $\mu$l final volume) and were incubated at 37° C. for 24 h. After the incubation, the supernatant was removed and wells were washed 3 times with 500 $\mu$l NaCl 0.9%, then fixated with 500 $\mu$l methanol for 10 min at RT. Methanol was then removed and the plate was dried at 37° C. for 15 min. Finally, the remaining cells in the well were stained with 1% crystal violet for 15 min at RT, washed 3 times with sterile $MQ-H_2O$. Stained cells were diluted in 33% (v/v) acetic acid and the absorbance was measured at 595 nm. All measurements were done by triplicate and in sterile conditions.

Figure 3:
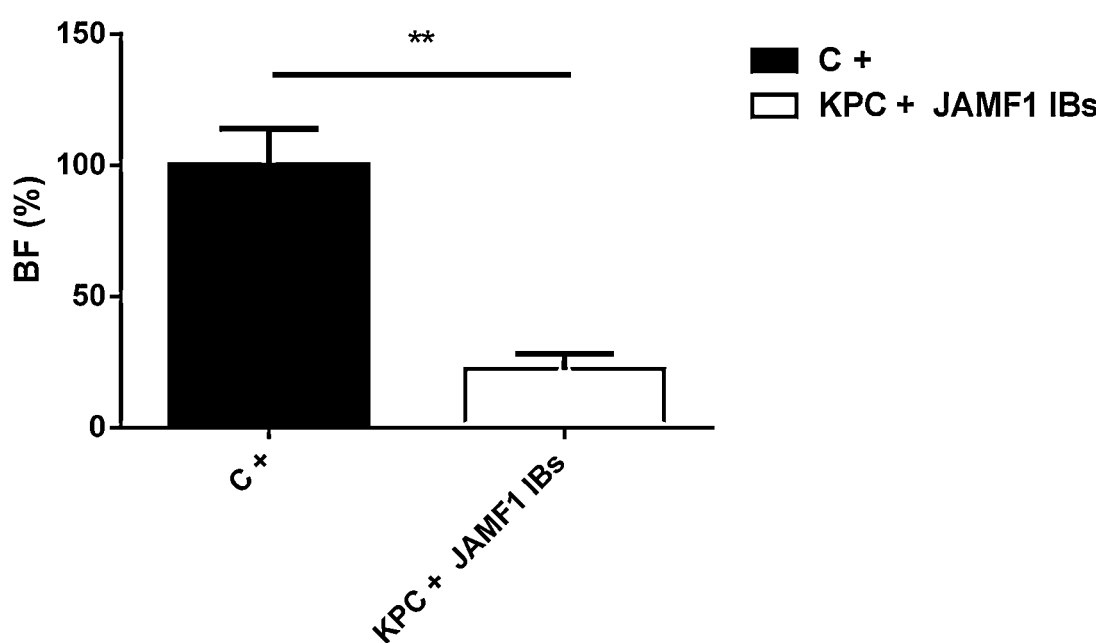
FIG. 3. Biofilm formation: Biofilm formation of *Klebsiella pneumoniae* Carbapenem resistant (KPC) in presence of immobilized JAMF1 IBs at 37° C. ON. BF=Biofilm formation, C+=KPC biofilm, KPC+IBs=KPC biofilm formation in microtiter plate coated with JAMF1 IBs. **P<0.05. See working Example 6 herein for further details.

Results and conclusions: This study shows (FIG. 3) that IBs were able to inhibit cell growth when they are immobilized in a surface, obtaining a decrease of 78% in the biofilm formation. It can be concluded that IBs format is also active when deposited on a desired surface to inhibit biofilm formation, opening the number of applications of these nanostructured antimicrobials.

Example 7: Enzymatic Activity of JAMF2 IBs

Figure 4:
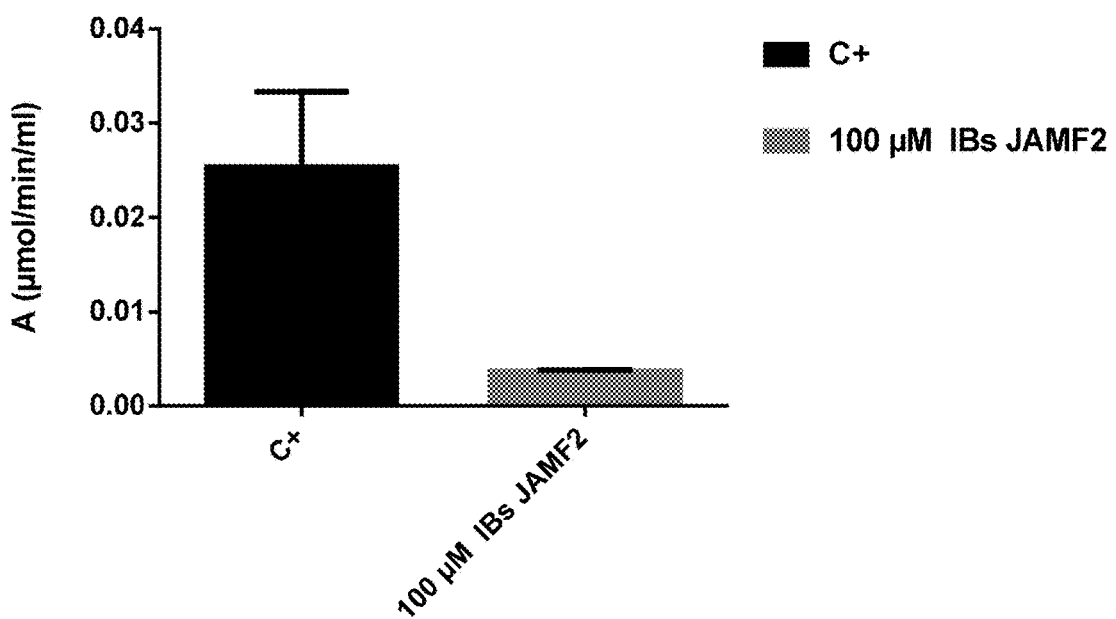
FIG. 4. Enzymatic activity of sPLA2 domain of JAMF2: Enzymatic activity of JAMF2 IB at room temperature (RT) ON. A=sPLA2 Activity, C+=Bee venom sPLA2. See working Example 7 herein for further details.

Aiming to explore the activity of another multidomain construct and using the enzymatic domain as a reporter, JAMF2 was designed (using other domain sequences) and its enzymatic activity was determined, as detailed in FIG. 4.

A fluorometric assay kit was used to measure sPLA2 activity (Cayman, Ann Arbor, MI, USA). Briefly, a PLA2 substrate consisting of 1,2-dithio analog of diheptanoyl phosphatidylcholine was used. Upon enzymatic hydrolysis of the thioester bond at the sn-2 position, free thiols were detected using 5,5'-dithio-bis-(2-nitrobenzoic acid) (DTNB) at 415 nm. Absorbance measurements were taken each 10 minutes ON. From the absorbance change per minute of the linear portion of the curve the reaction rate ($\mu$mol/min/ml) can be determined using the DTNB extinction coefficient. At least 8 time points were used for the calculations.

Results and conclusions: This assay shows (FIG. 4) that JAMF2 also had enzymatic activity when produced as IBs. It is proved again that this assay is a fast system to determine the activity of the enzymatic domain of the multidomain polypeptides of the invention.

Example 8: Obtaining Soluble Protein from IBs

Figure 5:
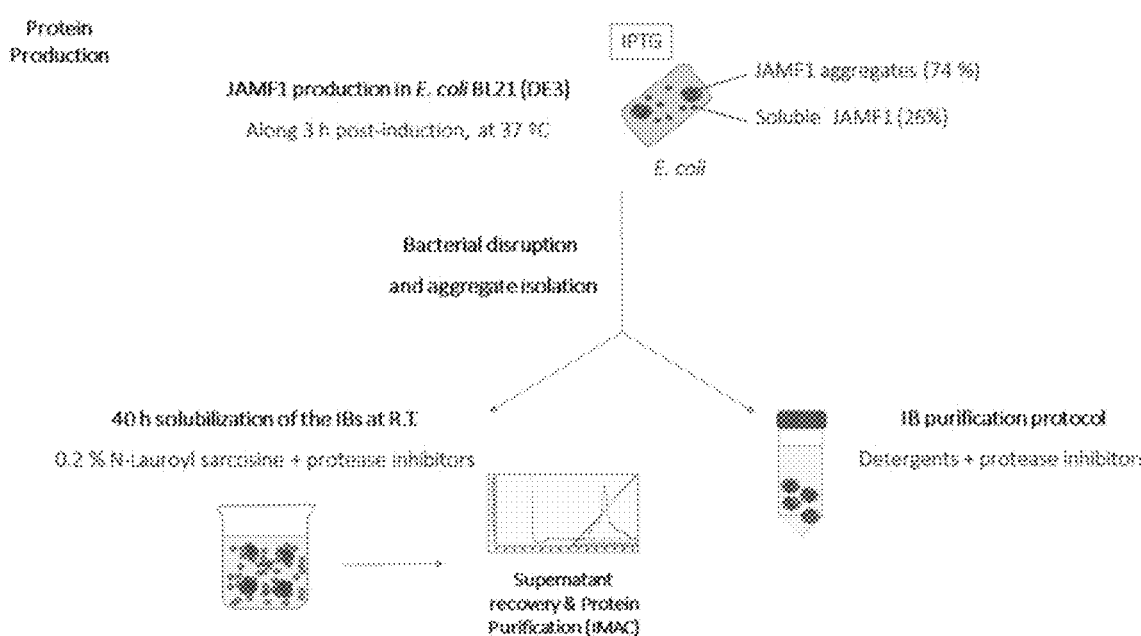
FIG. 5: IB production, purification and mild extraction protocol for obtaining soluble protein from IBs. See working Example 8 herein for further details.

Since the multidomain protein contain a purification tag, it is possible to use the IBs as a source to obtain soluble protein after a mild extraction protocol (in non-denaturing conditions). Depending on the final application a purer and soluble format could be better than a more stable and slow-release format (IBs). A scheme of the steps of the protocol is shown in FIG. 5.

To obtain solubilized protein from IBs, 2 l of JAMF1 and 2 l of JAM2 cultures were produced in *E. coli* BL21 (DE3). Inductions were conducted for 3 h. The whole volumes were centrifuged at 6,000×g and the pellets were resuspended in 120 ml of PBS 1× in presence of protease inhibitors. Samples were subjected to 4 rounds of sonication for 5 minutes at 10% amplitude under 0.5 s cycle, intercalated by a minimum of 5 min in ice. Protein pellets were recovered and washed once with distilled water. Pellets were weighted and solubilized in 0.2% N-lauroyl sarcosine and 40 mM Tris at a ratio of 40 ml/g of wet pellet as described by Peternel 2008 and adding protease inhibitors. The mixture was incubated 40 h ON at RT under agitation and the supernatant was recovered through centrifugation at 15,000×g for 45 min at 4° C. for further purification. NaCl and imidazole were added to the solubilized proteins to equilibrate the samples with the binding buffer composition, and IMAC purification was carried in an ÄKTA purifier FPLC (GE Healthcare) using 1 ml HisTrap HP columns (GE Healthcare). Both the binding and the elution buffer contained 0.2% N-lauroyl sarcosine, and the final imidazole concentration in the elution buffer was 0.5 mM. The buffer of the selected fractions was changed to KPi using a desalting column (GE Healthcare). The amount of purified protein was determined by Bradford's assay using BSA as calibration curve, and the integrity of the protein analyzed by SDS-PAGE.

Example 9: Purity, Yield and Aggregation of JAMF1 IBs and the Solubilized and Purified JAMF1

Figure 6A:
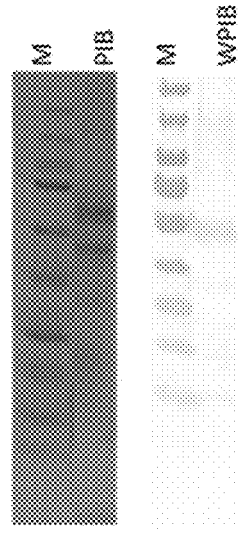
FIG. 6A: Purity, yield and aggregation of JAMF1 IBs.
Figure 6B:
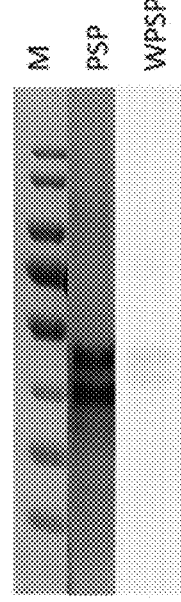
FIG. 6B: the solubilized and purified JAMF1: Protein gels of the purified JAMF1 IBs and the solubilized and purified JAMF1. M=Marker, PIB=Purified IBs, WPIB=Western blot of purified IBs, PSP=Purified solubilized protein, WPSP=Western blot of purified soluble protein, ST=Bacterial strain, Y=Protein yield in mg/l of Culture, P=Protein purity, AG=Percentage of aggregated protein. See working Example 9 herein for further details.

JAMF1 IBs (FIG. 6A) and IMAC purified solubilized protein (FIG. 6B) were analyzed by denaturing SDS-PAGE (15% acrylamide). Denaturing buffer (Laemli 4×: Tris base 1.28 g, glycerol 8 ml, SDS 1.6 g, β-mercaptoethanol 4 ml, urea 9.6 g in 20 ml) was added to the IBs and solubilized fractions to a final concentration of 1×. Soluble protein and IBs were boiled for 10 and 45 min, respectively. At that time, samples were loaded onto the gel. SDS-PAGE protein bands were transferred onto PVDF membranes and identified using a commercial anti-his antibody (1:1,000, sc-57598, Santa Cruz Biotechnology, Santa Cruz, CA, USA), followed by an incubation with a secondary ALP-conjugated anti-mouse IgG (whole molecule) antibody (Sigma-Aldrich) at a dilution of 1:20,000. The amounts of recombinant protein were estimated by comparison with known amounts (usually ranging from 125 to 1000 ng) of T22-GFP-His protein (previously described in Unzueta et al., 2012). Protein bands were visualized with a solution of NBT/BCIP (B6404, Sigma-Aldrich), and images were obtained using a Color Image Scanner. ImageJ software was used to perform densitometric analyses of the bands.

Results and conclusions: The results of this analysis are summarized in tables (FIGS. 6A and 6B), where the purity and the yield obtained for both IBs and protein solubilized and purified using IBs as protein source have been determined. JAMF1 IBs represents the 74% of the total protein overproduced and after the purification protocol we obtained a yield of 96.5 mg/l of bacterial culture and a purity of 95%. Besides, the yield and the purity of the solubilized protein once purified are 0.67 mg/l and 93%, respectively. IBs obtained are produced at good rates and are also an optimal source obtaining solubilized and purified protein.

Example 10: Purity, Yield and Aggregation of JAMF2 IBs and the Solubilized and Purified JAMF2

Figure 7A:
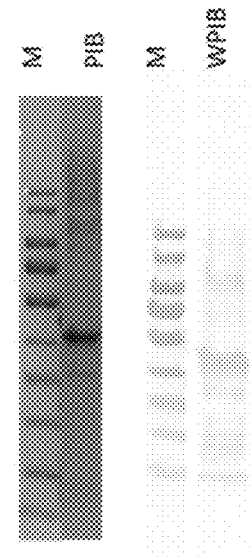
FIG. 7A: Purity, yield and aggregation of JAMF2 IBs.
Figure 7B:
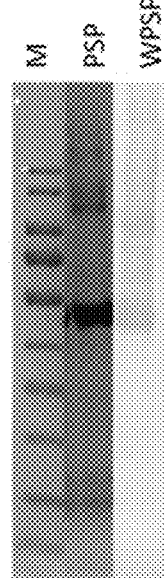
FIG. 7B: the solubilized and purified JAMF2: Protein gels of the purified JAMF2 IBs and the solubilized and purified JAMF2. M=Marker, PIB=Purified IBs, WPIB=Western blot of purified IBs, PSP=Purified solubilized protein, WPSP=Western blot of purified soluble protein, ST=Bacterial strain, Y=Protein yield in mg/l of Culture, P=Protein purity, AG=Percentage of aggregated protein. See working Example 10 herein for further details.

JAMF2 IBs (FIG. 7A) and IMAC purified solubilized protein (FIG. 7B) were analyzed by denaturing SDS-PAGE (15% acrylamide). Denaturing buffer (Laemli 4×: Tris base 1.28 g, glycerol 8 ml, SDS 1.6 g. β-mercaptoethanol 4 ml, urea 9.6 g in 20 ml) was added to the IBs and solubilized fractions to a final concentration of 1×. Soluble protein and IBs were boiled for 10 and 45 min, respectively. At that time, samples were loaded onto the gel. SDS-PAGE protein bands were transferred onto PVDF membranes and identified using a commercial anti-his antibody (1:1,000, sc-57598, Santa Cruz Biotechnology, Santa Cruz, CA, USA), followed by an incubation with a secondary ALP-conjugated anti-mouse IgG (whole molecule) antibody (Sigma-Aldrich) at a dilution of 1:20,000. The amounts of recombinant protein were estimated by comparison with known amounts (usually ranging from 125 to 1000 ng) of T22-GFP-His protein (previously described in Unzueta et al., 2012). Protein bands were visualized with a solution of NBT/BCIP (B6404, Sigma-Aldrich), and images were obtained using a Color Image Scanner. ImageJ software was used to perform densitometric analyses of the bands.

Results and conclusions: The results of this analysis are summarized in tables (FIGS. 7A and 7B), where the purity and the yield obtained for both IBs and protein solubilized and purified using IBs as protein source have been determined. JAMF2 IBs represents the 88% of the total protein overproduced and after the purification protocol we obtained a yield of 179.2 mg/l of bacterial culture and a purity of 88%. Besides, the yield and the purity of the solubilized protein once purified are 0.34 mg/l and 89%, respectively. IBs obtained are produced at good rates and are also an optimal source for the obtention of solubilized and purified protein.

Example 11: Antibacterial Activity Assay Comparing Solubilized JAMF1 and JAMF2

The antibacterial assay as well as the enzymatic assay were performed with solubilized and purified JAMF1 and JAMF2 proteins to demonstrate that different sequences in the peptidic domains have antimicrobial activity.

*E. coli* strains were grown in Luria-Bertani (LB) medium (w/v): 0.5% yeast extract, 1% tryptone and 1% NaCl; Bacterial cultures were grown at 37° C. in their corresponding growing medium until the $OD_{600}$ was 0.4-0.6 and subsequently diluted to obtain 10 million colony-forming units (CFU) per ml in sterile KPi buffer. 100 µl from this dilution ($10^6$ CFUs) were centrifuged at 6,000×g for 15 min at 4° C. and the supernatant was removed. After that, either 100 µl of KPi buffer (Control) or 100 µl of KPi buffer containing antimicrobial protein concentrations ranging from 0 to 1 M were added. Then, bacterial cultures were incubated for 16 h at 37° C. Then cultures were then serially diluted using KPi buffer and plated in LB-agar dishes. After a 16 h incubation at 37° C., individual colonies of bacteria were counted manually. For each concentration of antimicrobial protein, the ratio of colonies counted to the number of colonies present on the control plate (0 µM) was calculated. Each condition was tested by triplicate and expressed as the average percentage of viable cells compared to the control.

Figure 8:
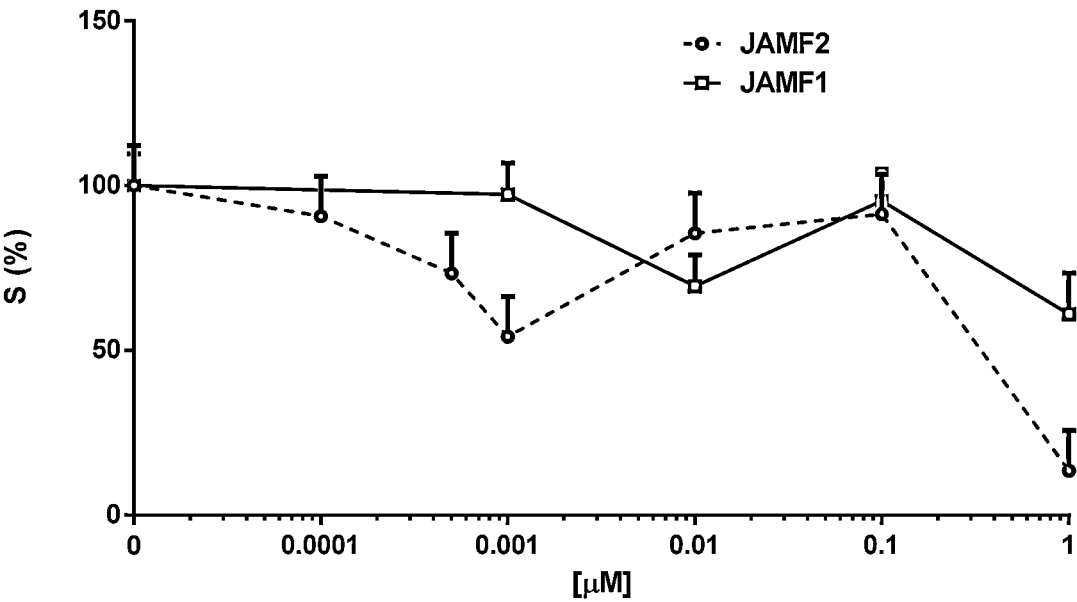
FIG. 8: Antibacterial activity assay comparing solubilized JAMF1 and JAMF2: Survival of *E. coli* DH5a strain in presence of JAMF1 or JAMF2 IBs at 37° C. ON. S=Bacterial survival in %. See working Example 11 herein for further details.

Results and conclusions: This study shows (FIG. 8) the antimicrobial activity of JAMF1, JAMF2 solubilized IBs incubated with *E. coli* DH5a. Different protein concentrations were tested observing an optimal range between 0.5 and 5 µM, where the growth inhibition reached values of 81% for JAMF1 and 86% for JAMF2, respectively. FIG. 8 shows that it is possible to design and produce different multidomain protein as IBs and its solubilized derived proteins with antimicrobial activity. Thus, this allows us to conclude that the different domains of the proteins can be tuned to create a final construct with the desired activity.

Example 12: Enzymatic Activity of sPLA2 Domain of Solubilized JAMF1 and JAMF2

A fluorometric assay kit was used to measure sPLA2 activity (Cayman, Ann Arbor, MI, USA). Briefly, a PLA2 substrate consisting of 1,2-dithio analog of diheptanoyl phosphatidylcholine was used. Upon enzymatic hydrolysis of the thioester bond at the sn-2 position, free thiols were detected using 5,5'-dithio-bis-(2-nitrobenzoic acid) (DTNB) at 415 nm. Absorbance measurements were taken each minute during 15 min. From the absorbance change per minute of the linear portion of the curve the reaction rate (μmol/min/ml) can be determined using the DTNB extinction coefficient. At least 8 time points were used for the calculations.

Figure 9:
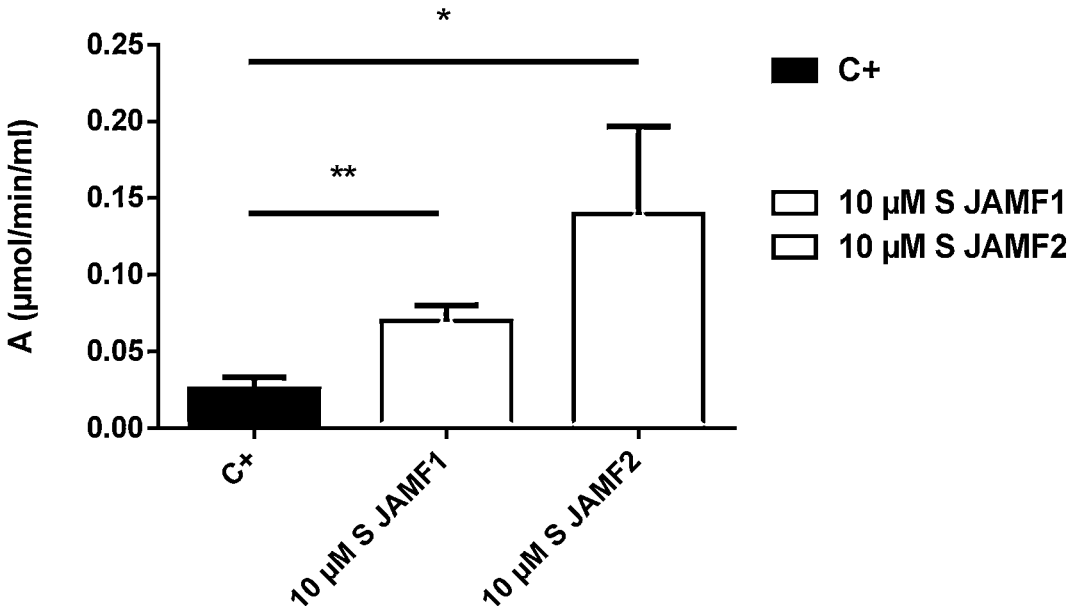
FIG. 9: Enzymatic activity of sPLA2 domain of solubilized JAMF1 and JAMF2: A=sPLA2 Activity, C+=Bee venom sPLA2, S=Solubilized. *P<0.05, **P<0.01. See working Example 12 herein for further details.

Results and conclusions: This assay shows (FIG. 9) that the two multidomain proteins when solubilized and purified from IBs have enzymatic activity. The solubilized version has an activity higher than the control used in this assay. This assay is also an optimal system for the fast detection of the activity of the enzymatic domain of the solubilized version of our multidomain proteins. Comparing the IB and solubilized protein activity, it is observed that IB format requires longer times to achieve its activity since the protein is embedded in a slow-release format.

Example 13: Antibacterial Activity Assay Comparing Solubilized JAMF1 and JAMF2 with Synthetic HD5 Single Domain and Recombinant HD5GFP The antibacterial assay was performed with solubilized and purified JAMF1 and JAMF2 to demonstrate that these multidomain proteins present greater antimicrobial activity than single antimicrobial domains based on synthetic HD5 or recombinant HD5 fused to a non-functional carrier such as GFP (HD5GFP).

To assess the bacterial cell viability, the BacTiter-Glo™ assay was conducted according to the manufacturer's protocol (BacTiter-GLO™ Microbial Cell Viability Assay, Promega, Mannheim, Germany). Shortly, *Klebsiella pneumoniae* Carbapenem-resistant (KPC) were grown O/N at 37° C. and 250 rpm in an appropriate medium and then diluted 1:100 in KPi buffer. Then, 150 UL from the KPi diluted cells were centrifuged in 1 mL tubes at 6,200×g at 4° C. for 15 min. Subsequently, the supernatant was removed and the pelleted cells were then resuspended with 150 μL of either KPi buffer (negative control) or 150 μL of JAMF1, JAMF2, HD5, and HD5GFP at 1 μM. After 5 h incubation at 37° C. in a 96-well plate, 100 UL were taken and mixed with 100 μL of the BacTiter-Glo™ reagent. Finally, luminescence was measured in a microplate luminometer (LUMIstar®, BMG LABTECH. Ortenberg, Germany). The measured arbitrary luminescence values were normalized against the control (KPi treatment).

Figure 10:
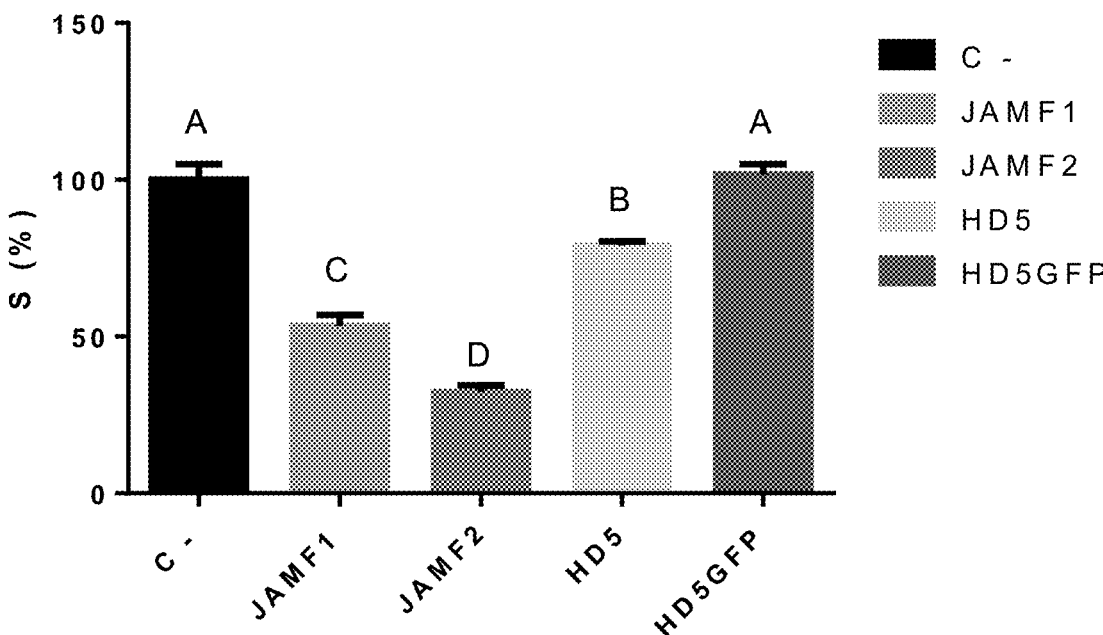
FIG. 10: *Klebsiella pneumoniae* Carbapenem resistant (KPC) survival percentage(S) after incubation with 1 μM of either solubilized multidomain proteins JAMF1 and JAMF2 or synthetic HD5 and HD5GFP protein. See working Example 13 herein for further details.

Results and conclusions: This study is a replicate of the antimicrobial activity of JAMF1 and JAMF2 described in Example 11 but here compared with the performance of single antimicrobial domain HD5 when produced as a synthetic peptide or fused to GFP protein (HD5GFP). FIG. 10 shows that the multidomain proteins JAMF1 and JAMF2 (containing in their sequence HD5 antimicrobial domain) have a much greater antibacterial activity than single domain HD5, even against an antibiotic resistant bacteria such as *Klebsiella pneumoniae* Carbapenem-resistant (KPC). The presence of several domains in JAMF proteins enhances the antimicrobial potential of HD5 domain.

Example 14: Anti-Infective Activity Assay, Based on IL-8 Activation, Comparing Solubilized JAMF1 and JAMF2 with Synthetic HD5 Single Domain and Recombinant HD5GFP Human adenocarcinoma colonic epithelial cell lines HT29 (gifts from Dr. K. Chadee, University of Calgary)

were grown in Dulbecco's modified Eagle's medium (Gibco, Life Technologies, Burlington, ON, Canada) with 10% fetal bovine serum (BenchmarkGemini BioProducts, Sacramento, CA, USA), 1 mM sodium pyruvate (Gibco, Life Technologies) and penicillin (100 U ml-1)/streptomycin (100 μg ml-1; HyClone Thermo, Fisher Scientific, Whitby, ON, Canada) in a humidified environment of 95% air and 5% $CO_2$ at 37° C. Cells were seeded in 24-well plates (Greiner Bio-One, Monroe, NC, USA) and cultured until they were 80-90% confluent. An infection was simulated in HT29 cells with LPS (1 μg/mL) and the antimicrobial effect of HD5 present in JAMF1 protein compared to HD5 synthetic peptide (Peptanova) and recombinant HD5 fused to GFP reporter (HD5GFP) protein was assessed at 0.1 μM for 24 h. The antimicrobial effect was here monitorized through the stimulation of IL-8 in HT29 cells, being IL-8 a chemokine responsible to recruit neutrophils and phagocytes that kill pathogen bacteria. For IL-8 quantification, supernatants were collected from cells and levels of IL-8 were determined using DuoSet ELISA kit (DY208, R & D Systems, Minneapolis, MN, USA) according to manufacturer's instructions.

Figure 11:
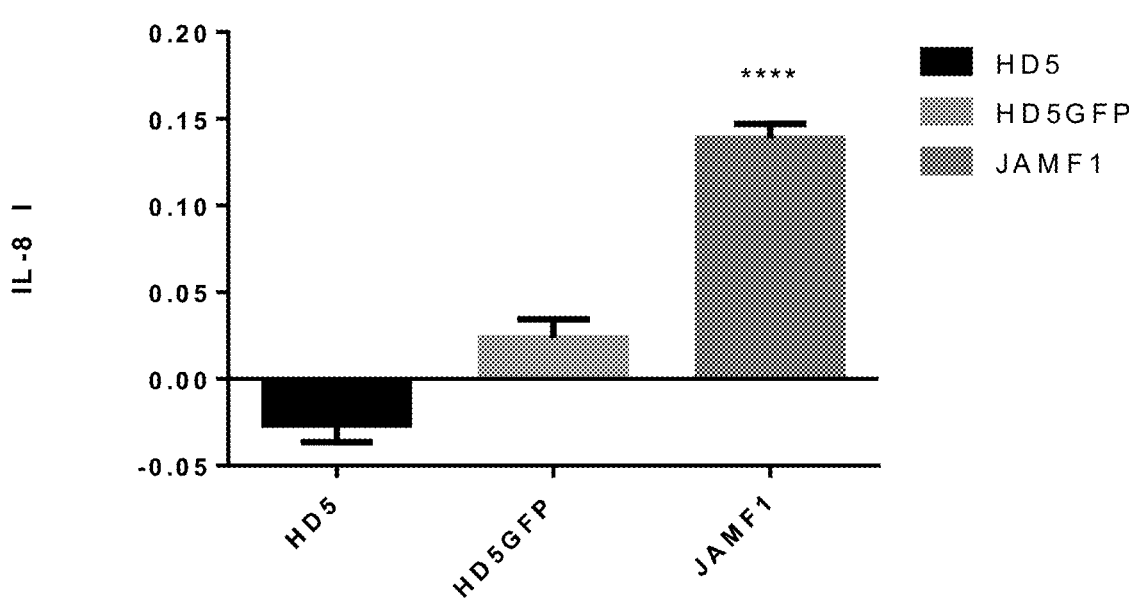
FIG. 11: Increase of IL-8 production (IL-8 I) in HT-29 cells stimulated with 1 μg/mL LPS in presence of 0.1 μM of antimicrobial proteins and peptides (JAMF1, synthetic HD5, HD5GFP fusion protein) compared with HT-29 cells only treated with LPS. See working Example 14 herein for further details.

Results and conclusions: This study compares (FIG. 11) the capacity of the domain HD5 included in the multidomain protein JAMF1 with the single domain HD5, either presented as a synthetic peptide (HD5, Peptanova) or fused with a non-functional carrier (GFP protein) (HD5GFP). Herein, the antimicrobial effect analyzed is based on the capacity of JAMF1, HD5 and HD5GFP to stimulate the synthesis of IL-8 in eukaryotic cells submitted to an infection stimulus. The results clearly show a better performance of HD5 presented in JAMF1 compared with that shown by HD5 and HD5GFP. These results confirm that the function of HD5 is enhanced in the multidomain protein JAMF1.

Example 15: Antitoxicity Role of Aggregation Sequences Jun and Fos in the Host Producer Strain

*E. coli* BL21 (DE3)/pET22b-JAMF1, *E. coli* BL21 (DE3)/pET22b-JAMF2, and *E. coli* BL21 (DE3)/pET22b-AM2 cultures were inoculated at an initial optical density ($OD_{600}$) of 0.05. Each culture was grown at 37° C. and 250 rpm in LB broth with 100 μg/ml of ampicillin to prevent plasmid loss. Protein expression was induced by 1 mM isopropyl-β-d-thiogalactoside (IPTG) when the $OD_{600}$ was 0.4-0.6. Cultures were grown 3 h post-induction and the growth of the host cell BL21 producing the proteins was monitorized at OD 600 nm.

Figure 12:
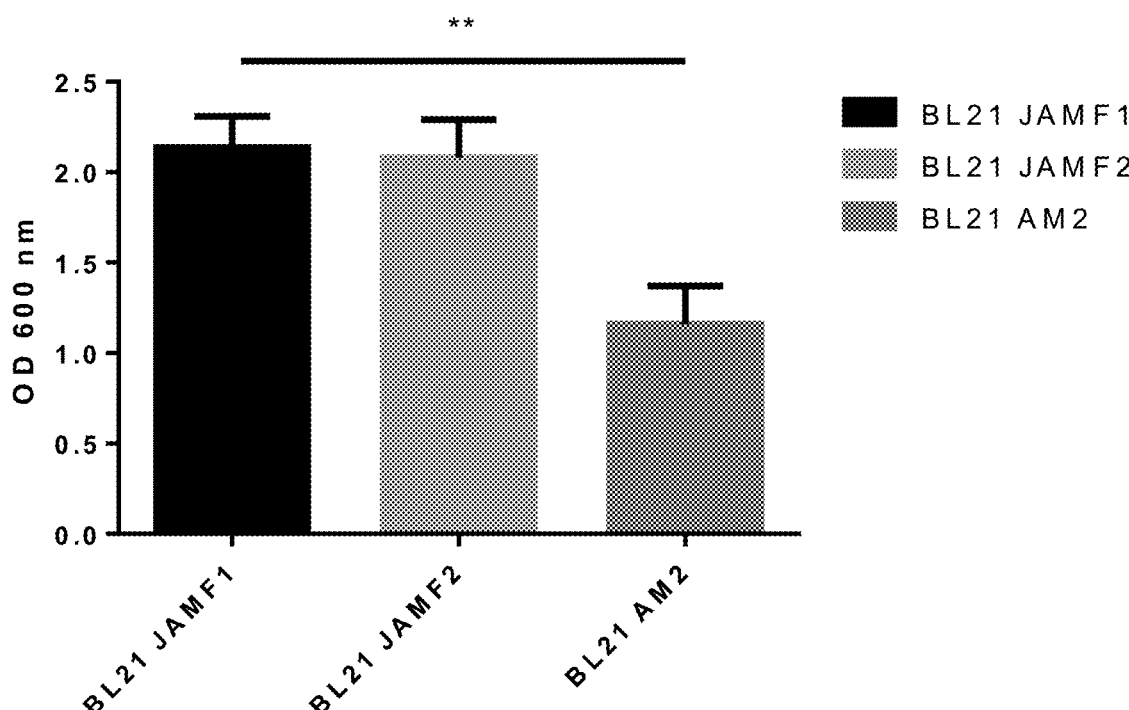
FIG. 12: Biomass measure ($OD_{600}$) of *Escherichia coli* BL21 at 3 h of producing proteins JAMF1 and JAMF2, containing aggregation tags Jun and Fos, and the protein AM2, without the mentioned tags. See working Example 15 herein for further details.

Results and conclusions: The multidomain proteins JAMF1 and JAMF2 contain aggregation tags Jun and Fos, as previously described in the present document. The sequence AM2 is equal than JAMF2 sequence but without Jun and Fos tags. Since the $OD_{600}$ is an indirect measure of bacterial biomass, the results of FIG. 12 indicate that AM2 expression is more toxic than JAMF1 and JAMF2 expression for the BL21 producer cells and suggest that sequences Jun and Fos could be a protective strategy of those toxic effects commonly observed during the production of antimicrobial proteins.

REFERENCES

Non-Patent Literature

Unzueta, U. et al, "Intracellular CXCR4+ cell targeting with T22-empowered protein-only nanoparticles" International Journal of Nanomedicine 2012 vol. 7 pp. 4533-4544

Smet K. et al., "Human antimicrobial peptides: defensins, cathelicidins and histatins" Biotechnology Letters 2005 vol. 27 pp. 1337-1347
Peternel S. et al., "Engineering inclusion bodies for non denaturing extraction of functional proteins" Microb Cell Fact. 2008 1; 7:34
Orrapin S. et al., "Recombinant expression of novel protegrin-1 dimer and LL-37-linker-histatin-5 hybrid peptide mediated biotin carboxyl carrier protein fusion partner" Protein expression and purification 2013 vol. 93 pp. 46-53

PATENT LITERATURE

U.S. Pat. No. 8,003,348 B2
WO2008030988 A2
WO2014078373 A1

---

The invention claimed is:

1. A recombinant antimicrobial multidomain polypeptide comprising at least three peptidic domains:
    a) a non-enzymatic antimicrobial peptidic domain from mammal's immune system,
    b) a bacterial binding peptidic domain which interacts with the bacterial cell wall or membrane, and
    c) an enzymatic antimicrobial peptidic domain from mammal's immune system; wherein:
    a) the non-enzymatic antimicrobial peptidic domain from mammal's immune system is selected from the group consisting of: a defensin, a histatin, and a cathelicidin;
    b) the bacterial binding peptidic domain is gelsolin or a gelsolin fragment; and
    c) the enzymatic antimicrobial peptidic domain from mammal's immune system is selected from the group consisting of: a secretory phospholipase, a lactoferrin, a transferrin, a lactotransferrin, and a lysozyme.

2. The polypeptide according to claim 1, further comprising at least one aggregation tag, wherein the aggregation tag is located at N-terminal end or C-terminal end of the polypeptide.

3. The polypeptide according to claim 2, comprising two aggregation tags which are complementary domains, one tag being located at N-terminal end and the other tag being located at C-terminal end, thereby flanking the polypeptide.

4. The polypeptide according to claim 1, wherein
    a) the non-enzymatic antimicrobial peptidic domain from mammal's immune system is a human defensin 5;
    b) the bacterial binding peptidic domain is gelsolin; and
    c) the enzymatic antimicrobial peptidic domain is secretory phospholipase A2.

5. The polypeptide according to claim 1, further comprising at least a purification tag.

6. The polypeptide according to claim 1, comprising an amino acid sequence selected from the group consisting of: a sequence which has at least a 85% identity to the sequence SEQ ID NO: 10, a sequence with SEQ ID NO: 10, a sequence which has at least a 85% identity to the sequence SEQ ID NO: 11, and a sequence with SEQ ID NO: 11, wherein the polypeptide has antimicrobial activity.

7. The polypeptide according to claim 1, which is in form of inclusion bodies.

8. Inclusion bodies comprising a recombinant antimicrobial multidomain polypeptide as defined in claim 1.

9. A pharmaceutical or veterinary composition comprising a recombinant antimicrobial multidomain polypeptide as defined in claim 1, and an acceptable carrier, diluent or excipient.

10. The polypeptide according to claim 1, wherein the gelsolin fragment comprises at least amino acids 188 to 196 of Uniprot P06396 (RLFQVKGRR).

11. A DNA construct comprising a sequence encoding the antimicrobial multidomain polypeptide according to claim 1.

12. A process for the production of the recombinant antimicrobial multidomain polypeptide of claim 1 which involves expression of the polypeptide as a heterologous protein in bacterial expression cells, wherein the polypeptide is accumulated in inclusion bodies, the process comprising the steps of:
    i) growing bacterial expression cells which comprise a DNA construct codifying for the antimicrobial multidomain polypeptide;
    ii) inducing the expression of the DNA construct by a specific inducer and further incubating the bacterial cells;
    iii) lysing the bacterial cells by means of a mechanical and/or enzymatic disruption method; and
    iv) purifying the inclusion bodies by washing with buffers and/or detergents.

13. The process of claim 12, further comprising:
    v) solubilizing the inclusion bodies to obtain the soluble polypeptide in mild conditions with detergent and/or buffer incubations; and
    vi) separating the soluble polypeptide by chromatography.

14. An antimicrobial agent for disinfecting medical and surgical materials, the antimicrobial agent comprising the recombinant antimicrobial multidomain polypeptide of claim 1.

15. The antimicrobial agent of claim 14, wherein the recombinant antimicrobial multidomain polypeptide is in the form of inclusion bodies.

16. A medicament composition comprising the recombinant antimicrobial multidomain polypeptide of claim 1.

17. The medicament composition of claim 16, wherein the recombinant antimicrobial multidomain polypeptide is in the form of inclusion bodies.

18. A method of treating and/or preventing bacterial infections in a mammal in need thereof, the method comprising administering the recombinant antimicrobial multidomain polypeptide of claim 1 to the mammal.

19. The method of claim 18, wherein the recombinant antimicrobial multidomain polypeptide is in the form of inclusion bodies.

20. An item impregnated with, coated in, or covered by a composition comprising the recombinant antimicrobial multidomain polypeptide of claim 1, wherein the item is selected from the group consisting of: a medical device, medical instrument, medical implement, prosthetic, implantable device or material, wound dressing, and a biologically compatible material.

21. The item of claim 20, wherein the recombinant antimicrobial multidomain polypeptide is in the form of inclusion bodies.

\* \* \* \* \*